US006268548B1

(12) United States Patent
Elthon et al.

(10) Patent No.: US 6,268,548 B1
(45) Date of Patent: Jul. 31, 2001

(54) ISOLATION AND CHARACTERIZATION OF GENE ENCODING MAIZE HEAT SHOCK PROTEIN

(75) Inventors: Thomas E. Elthon, Lincoln, NE (US); Adrian A. Lund, Niantic, CT (US); Dinakar Bhattramakki, Newark, DE (US); David Rhoads, Omaha, NE (US)

(73) Assignee: Board of Regents of University of Nebraska, Lincoln, NE (US)

( * ) Notice: Subject to any disclaimer, the term of this patent is extended or adjusted under 35 U.S.C. 154(b) by 0 days.

(21) Appl. No.: 09/249,180

(22) Filed: Feb. 12, 1999

Related U.S. Application Data
(60) Provisional application No. 60/076,014, filed on Feb. 26, 1998.

(51) Int. Cl.[7] .......................... C12N 15/29; C12N 15/82; C12N 15/09; C12N 5/05; A01H 5/00
(52) U.S. Cl. ................. 800/289; 800/320.1; 800/317; 800/320; 800/306; 800/298; 800/278; 435/320.1; 435/468; 435/419; 536/23.1; 536/23.6; 536/24.1
(58) Field of Search ..................... 800/289, 320.1, 800/317, 298, 278, 306, 320; 435/320.1, 468, 419; 536/23.1, 23.6, 24.1

(56) References Cited

U.S. PATENT DOCUMENTS

| 5,232,833 | 8/1993 | Sanders et al. ............... 435/7.21 |
|---|---|---|
| 5,789,180 | 8/1998 | Bernardin ..................... 435/7.8 |
| 5,922,929 | * 7/1999 | Zimmerman et al. ........... 800/278 |

OTHER PUBLICATIONS

Schoffl, F.; Baumann, G.; Raschke, E.; and Bevan, M.; "The Expression of Heat–shock Genes in Higher Plants"; 1986; pp. 111–126; Universitat Bielefeld, Fakultat fur Biologie, Bielefeld and Plant Breeding Institute, Cambridge, United Kingdom.
Lund et al. Plant physiology vol. 114, No. 3 p. 204, Aug. 1997.*
Schoffl et al. Phil. Trans. R. Soc. London B 314:453–468, 1986.*
Adrian A. Lund et al., "Heat Stress Response of Maize Mitochondria," *Plant Physiol*, vol. 116, 1998, pp. 1097–1110.
T. Maniatis, "Molecular Cloning: A Laboratory Manual," *Cold Spring Harbor Laboratory*, 1982, pp. 55–60.
James C. Carrington and Deon D. Freed, "Cap–Independent Enhancement of Translation by a Plant Potyvirus 5' Nontranslated Region," *J. Virol.*, vol. 64, No. 4, Apr. 1990, pp. 1590–1597.

Peter Hajdukiewicz et al., "The Small, Versatile pPZP Family of Agrobacterium Binary Vectors for Plant Transformation," 1994, pp. 989–994.
Eric Richards, "Preparation of Genomic DNA from Plant Tissue," *Current Protocols*, 1987, pp. 2.3.1–2.3.3.
Chu–Yung Lin et al., "Acquisition of Thermotolerance in Soybean Seedlings," *Plant Physiol.*, Vo. 74, 1984, pp. 152–160.
Mei Chou et al., "Thermotolerance of Isolated Mitochondria Associated with Heat Shock Proteins," *Plant Physiol.*, vol. 89, 1989, pp. 617–621.
Catherine Lenne and Roland Douce, "A Low Molecular Mass Heat–Shock Protein Is Localized to Higher Plant Mitochondria," *Plant Physiol.*, vol. 105, 1994, pp. 1255–1261.
Catherine Lenne et al., "Sequence and Expression of the mRNA Encoding HSP22, The Mitochondrial Small Heat–Sock Protein in Pea Leaves," *Biochem, J.*, vol. 311, 1995, pp. 805–813.
Peter R. LaFayette et al., "Molecular Characterization of cDNAs Encoding Low–Molecular–Weight Heat Shock Proteins of Soybeans," *Plant Molecular Biology*, vol. 30, 1996, pp. 159–169.
Elizabeth R. Waters, "Evolution, Structure and Function of the Small Heat Shock Proteins in Plants," *Journal of Experimental Botany*, vol. 47, No. 296, Mar. 1996, pp. 325–338.
Deanna A. Willett et al., "Nucleotide Sequence of a cDNA Encoding a Mitochondrion–Localized Small HSP from Arabidopsis Thaliana: AtHsp23.6 (Accession No. U72958)," (PGR96–117), *Plant Physiol.*, vol. 112:1399, 1996.
Jeong Hee Lee et al., "Derepression of the Activity of Genetically Engineered Heat Shock Factor Causes Constitutive Synthesis of Heat Shock Proteins and Increased Thermotolerance in Transgenic Arabidopsis," *The Plant Journal*, vol. 8, No. 4, 1995, pp. 603–612.

* cited by examiner

Primary Examiner—David T. Fox
Assistant Examiner—Medina A. Ibrahim
(74) Attorney, Agent, or Firm—James H. Marsh, Jr.; Shook, Hardy & Bacon LLP

(57) ABSTRACT

This invention relates to the identification and characterization of the maize HSP22 protein including the corresponding nucleic acid molecules, nucleic acid fragments and protein fragments. Further, this invention relates to both polyclonal and monoclonal antibodies to HSP22 and the production thereof. These antibodies can be used in a method for detecting the presence of HSP22 expression in whole leaf samples. Further, the nucleic acid molecule and fragments thereof can be used in assays to detect the levels of nucleic acid molecules involved in HSP22 expression. The levels of both HSP22 and HSP22 mRNA are then utilized as an indication of a plant's ability to tolerate heat stress. Additionally, plants can be transformed to express increased levels of HSP22.

17 Claims, 25 Drawing Sheets

Continuous Heat-Shock (hrs)

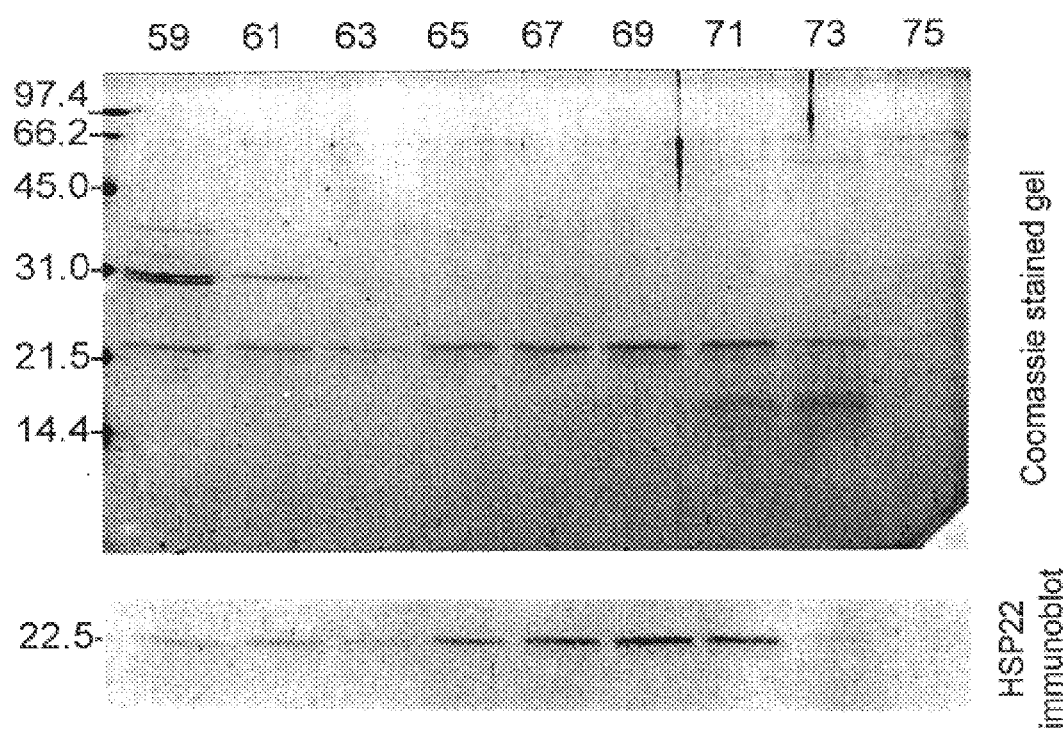

Figure 17 A. Mass spectrum of Peak 8
Figure 17 B. Transformation of Peak 8 mass spectrum
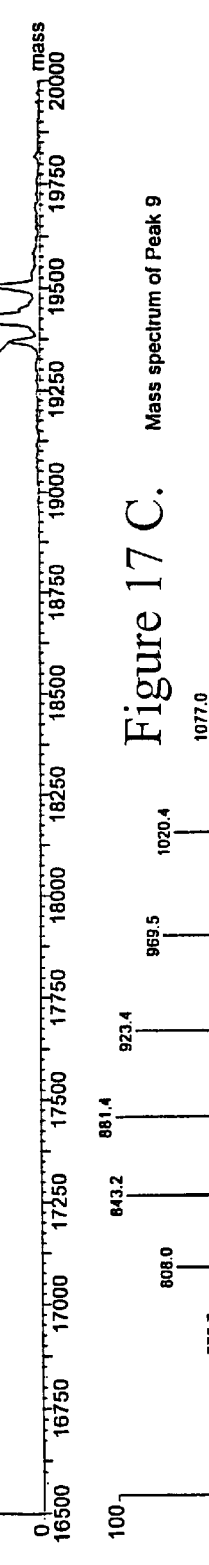
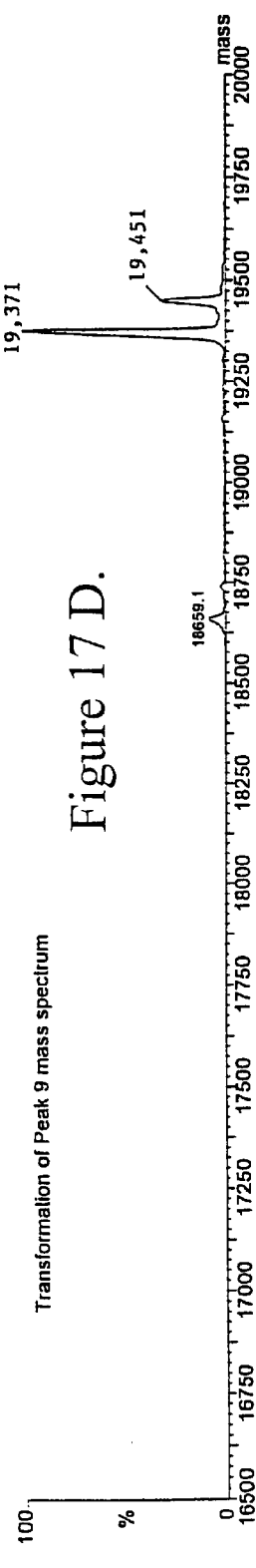
Figure 17 C. Mass spectrum of Peak 9
Figure 17 D. Transformation of Peak 9 mass spectrum

```
  1 CCACAACAGCGAAGGAGAAAGCAGACCAACCTAGCCACCCAGGGAGAAAGAGGCCAAAAG

61 GGAGGGGAGAGTGTCGTCATGGCTTCCATTGTCGCTTCCAGGAGGGCCGTTCCTCTAGTT
                    MetAlaSerIleValAlaSerArgArgAlaValProLeuVal

121 CGCGCTCTGGAGAAGCTCATCGCAGCGTCCTCCGCTCCCGGGACTGGCTCCGCCCTCAGG
    ArgAlaLeuGluLysLeuIleAlaAlaSerSerAlaProGlyThrGlySerAlaLeuArg

181 CCGGTGGCAGTCGCCGGCGGCCTCCGCGGCTACAACACCGGCGCTCCGCTCCGACGCTAC
    ProValAlaValAlaGlyGlyLeuArgGlyTyrAsnThrGlyAlaProLeuArgArgTyr

241 GAGGGGGCCGAGTCGGAAGACGATAGCGTCCGCGAGTACGATGGGCGGCACGGCGGCCGG
    GluGlyAlaGluSerGluAspAspSerValArgGluTyrAspGlyArgHisGlyGlyArg

301 GACTACGCTGTGCCCAGCCTGTTCTCAGATATTTTCCGTGATCCGCTTAGTGCGCCGCAC
    AspTyrAlaValProSerLeuPheSerAspIlePheArgAspProLeuSerAlaProHis

361 AGCATTGGCCGCCTGCTGAACCTTGTGGACGACTTGGCGGTGGCGGCGCCAGGTCGTGCG
    SerIleGlyArgLeuLeuAsnLeuValAspAspLeuAlaValAlaAlaProGlyArgAla

421 GTGCGCCGTGGCTGGAACGCGAAGGAGGACGAGGAGGCGCTGCACCTGAGGGTGGACATG
    ValArgArgGlyTrpAsnAlaLysGluAspGluGluAlaLeuHisLeuArgValAspMet

481 CCAGGCCTGGGGAAGGAGCACGTCAAGGTGTGGGCGGAGCAGAACAGCCTGGTGATCAAG
    ProGlyLeuGlyLysGluHisValLysValTrpAlaGluGlnAsnSerLeuValIleLys

541 GGCGAGGGCGAGAAGGAGGATAGCGAGGACGAGGCCGCCCCGCCTCCGAGATACAGCGGT
    GlyGluGlyGluLysGluAspSerGluAspGluAlaAlaProProProArgTyrSerGly

601 CGCATCGAGCTCGCGCCAGAGGTTTACAGGATGGACAAGATCAAGGCGGAGATGAAGAAC
    ArgIleGluLeuAlaProGluValTyrArgMetAspLysIleLysAlaGluMetLysAsn

661 GGCGTGCTCAAGGTGGTCGTGCCGAAGGTGAAGGAGCAGCAGCGCAAGGACGTGTTCCAA
    GlyValLeuLysValValValProLysValLysGluGlnGlnArgLysAspValPheGln

721 GTCAACGTCGAGTAGATGTTTCCAAATAGAAGCAAGTGCCGGTACGGGATGGAGGATTGG
    ValAsnValGluEnd

781 AGGGGCACTGCCAAACTAGGATTCCTCTCTCTCAATCTGATCTGGATTCTGGAATCAGAT

841 TTCTCTTCTTTCATTTTTCTCGTCTATCTTCTATCAGTATGAAATAAGCAACGTCGCTTC

901 AGTTTTCGTGTCAAGGCCGGTGGAGTCGCCTATGTTTATTTTATTTTCTTTGTATTTCCT

961 ACCTGGACACACGTTCTCTATGCCGTGTTTGGTTTCCGCAGATTTTTAAAATATGCATGT

1021 TCAAACCC 1028
```

Figure 19.

HSP22 Southern Blot Analysis

Maize B73 genomic DNA digests.

| Enzymes giving one band: | Size (kb): |
|---|---|
| KpnI | 22 |
| BglII | 20 |
| NcoI | 12 |
| XbaI | 7 |
| EcoRV | 5 |
| HindIII | 2.8 |
| BamHI | 1.0 |

Genomic DNA probed with mature HSP22 protein cDNA.

Binary Vector for Plant Transformation

ISOLATION AND CHARACTERIZATION OF GENE ENCODING MAIZE HEAT SHOCK PROTEIN

CROSS REFERENCE TO RELATED APPLICATIONS

This application claims the benefit of U.S. Provisional Application Ser. No. 60/076,014, filed on Feb. 26, 1998.

BACKGROUND OF THE INVENTION

The effect of environmental stress on agronomic plants has been a major focus of plant research. Plant productivity is related to the ability of plants to respond to and adapt to environmental stress (Sachs and Ho 1986). The proteins produced by higher plants in response to stress have been well-characterized (Key et al., 1981; Cooper and Ho, 1983; Sachs and Ho, 1986). Many stress proteins have recently been found to be chaperones, a class of proteins involved in the folding of newly synthesized proteins (Ellis and van der Vies, 1991; Gething and Sambrook, 1992; Craig et al., 1993). The chaperones have been proposed to function during stress in binding partially denatured proteins, thus preventing their degradation. Additionally, the chaperones assist in the refolding of these partially denatured proteins into their native structure in an ATP-dependent manner following the relief of stress (Rochester et al., 1986; Ellis and Hemmingsen, 1989; Hendrick and Hartl, 1993; Schröder et al., 1993). The two most extensively studied classes of chaperones are heat shock protein (HSP) 70 homologs and cpn60 homologs.

HSP70 homologs have been found in higher plant cytoplasm (Giorini and Galili, 1991), endoplasmic reticulum (Denecke et al., 1991), chloroplasts (Marshall et al., 1990; Ko et al., 20 1992; Marshall and Keegstra, 1992; Madueño et al., 1993; Wang et al., 1993), and mitochondria (Watts et al., 1992; Neuman et al., 1993). Genes for mitochondrial HSP70 are nuclearly encoded and have been isolated from pea (Watts et al., 1992), potato and tomato (Neuman et al., 1993).

The cpn60s are a group of ubiquitous proteins with a subunit size of approximately 60 kDa that share a functional and structural similarity to the tetradecameric *E. coli* GroEL complex (Gatenby, 1992). The maize and *Arabidopsis thaliana* mitochondrial cpn60 genes have been isolated and found to be encoded in the nucleus (Prasad and Stewart, 1992). The maize cpn60 was hypothesized to aid in the assembly of new mitochondrial protein complexes during the rapid organelle biogenesis of seedling germination and heterotrophic growth (Prasad and Stewart, 1992).

Neither the HSP70 homologs nor the cpn 60 homologs are very effective indicators of a heat resistant plant's ability to tolerate heat stress. However, there is another group of heat shock proteins that may be effective indicators. This group is the low molecular mass (17–30 kDa) HSPs (Waters et al., 1996). Recent reports have established that the cytosolic forms of plant small HSPs (sHSPs) can function as molecular chaperones in vitro (Lee et al., 1995a). Lenne and Douce (1994) identified a mitochondrial matrix-localized low molecular mass HSP identified as HSP22. Pea leaf mitochondrial HSP22 is conditionally expressed only at high temperatures and the protein level remained high for at least three days following heat stress (Lenne and Douce, 1994). A cDNA for pea mitochondrial HSP22 has been identified and establishes this protein as a member of the sHSP superfamily (Lenne et al., 1995). cDNAs for mitochondrial sHSPs have also been characterized in soybean (La Fayette et al., 1996), *A. thaliana* (Willett et al., 1996), and *Chenopodium rubrum* (Lenne et al., 1995; Waters et al., 1996). However, there has not been an sHSP isolated from a mitochondria of a heat resistant plant. For example, maize is a heat-resistant plant and is one of the world's greatest food sources. The isolation of an sHSP from maize would allow for testing of plants to determine their ability to tolerate heat stress resistance. This testing could take several forms if a sHSP were isolated. Additionally, vectors could be constructed containing the nucleic acid molecule for the sHSP.

There is a need for the discovery of an isolated sHSP protein from a heat resistant plant. This sHSP could be utilized to indicate a heat resistant plant's ability to tolerate heat stress. Additionally, if a sHSP were isolated from a heat resistant plant and cloned into an expression vector, there would be large quantities of HSP for research, the production of antibodies, and the generation of nucleic acid probes.

SUMMARY OF THE INVENTION

Accordingly, it is an object of the present invention to provide a method for determining a plant specie's ability to tolerate heat stress by comparing levels of HSP22 expression.

A further object of the present invention is to provide a combination comprising the necessary materials needed to determine a plant specie's ability to tolerate heat stress by comparing levels of HSP22 expression.

A further object of the present invention is to provide an isolated nucleic acid molecule encoding a protein that is expressed during heat stress conditions and that hybridizes, under stringent conditions, to SEQ. ID. NO. 7.

A further object of the present invention is to provide isolated protein comprising SEQ. ID. NO. 6.

A further object of the present invention is to provide an isolated nucleic acid molecule encoding a protein that is expressed during heat stress conditions and that hybridizes under stringent conditions to a nucleic acid molecule corresponding to an amino acid molecule of SEQ. ID. NO. 6.

A further object of the present invention is to provide fragments of the nucleic acid molecule encoding HSP22 that hybridize to SEQ. ID. NO. 7 and that code for products that have substantially the same physical characteristics as HSP22. These fragments can be either recombinant, synthetic, or a combination thereof.

A further object of the present invention is to provide a recombinant vector comprising a nucleic acid molecule encoding a protein that has physical characteristics substantially similar to HSP22. The definition of a vector for the purposes of this invention is any nucleic acid molecule into which a foreign nucleic acid molecule may be inserted wherein the nucleic acid molecule containing the foreign nucleic acid molecule may be used to introduce the foreign nucleic acid molecule into a host cell. This vector may also comprise regulatory elements operably linked to the nucleic acid molecule.

A further object of the present invention is to provide various cells transformed with a vector comprising a nucleic acid molecule encoding a protein that has physical characteristics substantially equal to HSP22. Addtionally, these cells could be plant cells capable of producing plants that have an increased ability to survive in heat stress conditions.

A further object of the present invention is to provide a methodology for the production of various products of the present invention. Examples include, but are not limited to, isolated nucleic acid molecules encoding HSP22, isolated HSP22, isolated SEQ. ID. NO. 7, isolated SEQ. ID. NO. 6, and the protein products of SEQ. ID. NO. 7.

Another object of the present invention is to provide novel and purified antibodies to HSP22. The antibodies can be polyclonal, monoclonal, or fragments thereof.

It is a further object of the present invention to provide a hybridoma for the production of HSP22 monoclonal antibodies.

It is a further object of the present invention to provide a method for the production of the hybridoma capable of producing monoclonal antibodies for HSP22.

By providing the above-stated objects, several advantages are realized. For example, plants can be screened for their ability to tolerate heat stress by comparing levels of HSP22 expression.

Another advantage realized by the present invention is the ability to screen plants with either antibodies to HSP22 or with nucleic acid probes that bind to HSP22 mRNA.

Still another advantage realized by the present invention is the ability to produce large quantities of HSP22, HSP22 antibodies, and HSP22 nucleic acids, for both commercial and scientific purposes.

Additional objects, advantages and novel features of the invention will be set forth in part in the description which follows and in part will become apparent to those skilled in the art upon examination of the following or may be learned by practice of the invention.

The mouse cell line HSP22 vector as described in this specification has been deposited with the American Type Cultural Collection (ATCC), Manassas, Va., USA. The deposit was filed with ATCC on Dec. 9, 1998. The vector is identified as mouse cell line HSP22, and by the ATCC accession No. CRL-1261 1. These deposited materials are available pursuant to all requirements of the United States Patent and Trademark Office.

BRIEF DESCRIPTION OF THE DRAWINGS

The accompanying drawings form a part of this specification and are to be read in conjunction therewith:

FIG. 15B depicts SDS-PAGE gels of the HSP22 containing fractions collected and stained with Coomassie blue. FIG. 15C depicts these fractions transferred to nitrocellulose and probed with affinity purified HSP22 polyclonal antibody;

FIG. 16B represents the total ion count which was taken by subjecting the sample to real time analysis on a VG Platform mass spectrometer utilizing an electrospray ionization source and a quadrapole analyzer with an eight second scan time from 700 to 1800 m/z. The first panel of FIG. 16C illustrates a Coomassie-stained SDS-PAGE gel of 20 μl from the sample that was applied to the column and of three fractions that were recovered (peaks 8, 9, and 10 in 16A). The middle panel of FIG. 16C is a similar gel which was immunoblotted with affinity purified HSP22 polyclonal antibodies. This blot demonstrates that both peak 8 and peak 9 contain HSP22. The right panel is the same gel of the middle panel after being recorded and then probed with cpn60B monoclonal antibody, revealing that cpn60 was present in the sample prior to chromatography and that it was not present in peaks 8, 9, and 10 after the chromatography;

FIGS. 17A–D are the mass spectral data from peaks 8 and 9, which were analyzed using the MassLinks software package. FIG. 17A is an analysis of peak 8 protein mass spectrum. The raw spectrum was transformed to reveal the masses of the proteins in peak 8 as illustrated in FIG. 17B. FIG. 17C is an analysis of peak 9 mass spectrum. FIG. 17D is the transformed data from peak 9 which reveals the masses of the proteins from peak 9;

FIG. 19 is a complete cDNA nucleotide molecule and protein translation for maize mitochondrial HSP22. A partial cDNA clone for HSP22, ZmHSP22P8 (P8), was isolated by screening a lambda phage cDNA expression library using the HSP22 monoclonal antibody. The library was constructed using mRNA from heat-stressed etiolated maize seedlings. The nucleotide molecule was completed using homologous overlapping molecules identified in the Pioneer Hi-Bred EST database. The mitochondrial transit peptide molecule and the 5' untranslated region of the cDNA were added from molecules CHSSH24R and CTSCG49R from the Heat Shock Recovery Seedling (8 h) and the Tassel Shoot EST libraries, respectively (underlined nucleotide sequence). The putative translational start is at nucleotide 79. The complete mitochondrial transit peptide is encoded from nucleotide 79 to 213. The mature HSP22 protein molecule is from nucleotide 214 to 735. The N-terminal amino acid molecule obtained from spot HSP22B is illustrated in bold type. The amino acid molecule from spot HSP22A is identical to the first 13 residues of the molecule from spot HSP22B (bold and underlined type). The identity of the $18^{th}$ residue ($Ser^{63}$) from spot HSP22B could not be determined during the Edman degradation. The 3' untranslated region is from 736 to 1028 plus a 15 nt polyadenylated tail;

DETAILED DESCRIPTION OF THE INVENTION

Figure 1:
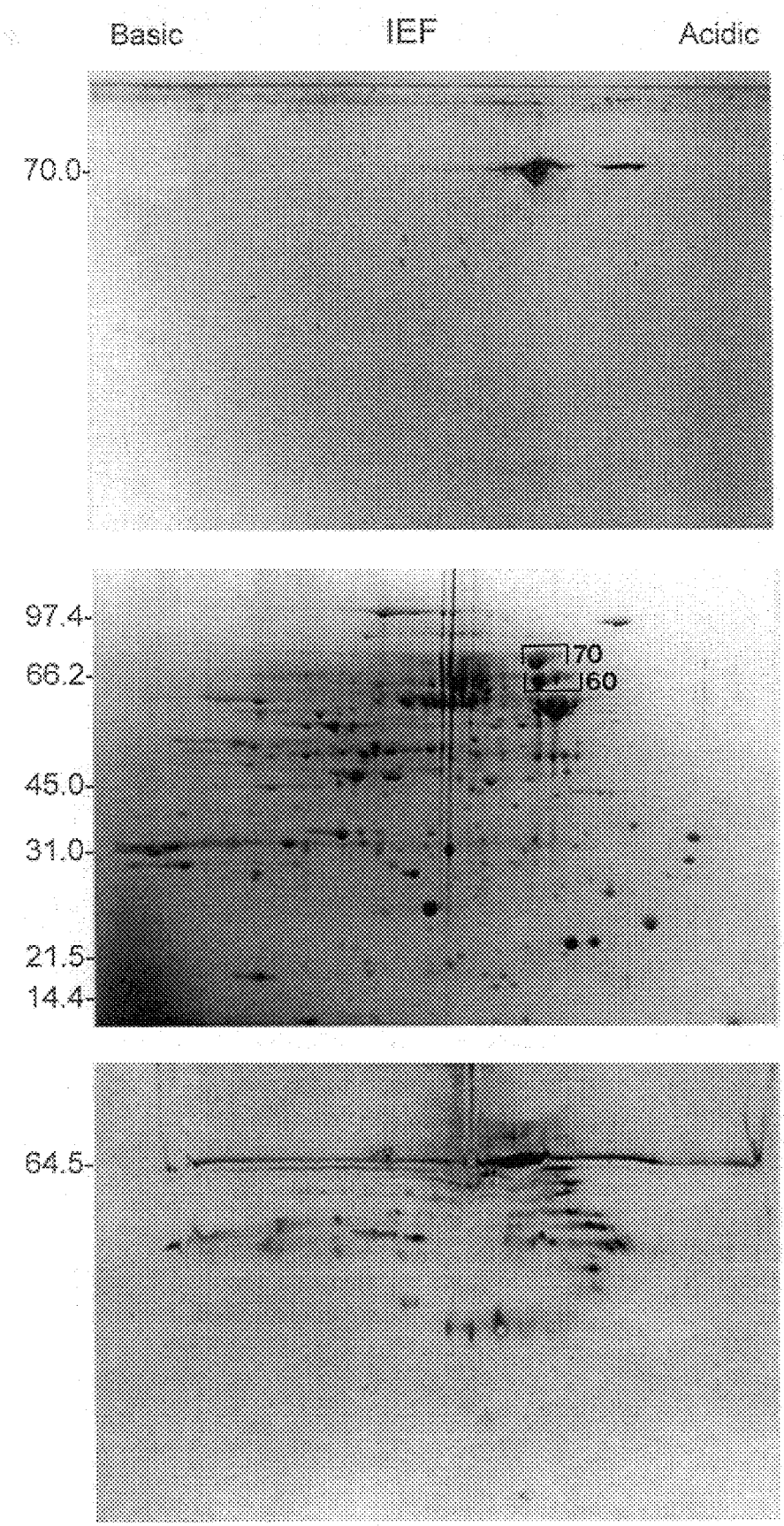
FIG. 1 illustrates the identification of *E. coli* DnaK (HSP70) and cpn60 protein homologs in maize mitochondria using two-dimensional SDS-PAGE and immunoblots. Two-dimensional gels were prepared with approximately 300 μg of maize mitochondrial protein and were either stained with Coomassie Brilliant Blue R-250 or blotted to nitrocellulose. Approximate molecular mass markers are on the left (kD). The top panel is a two-dimensional immunoblot probed with polyclonal antisera against *E. coli* DnaK. The middle panel is a similar two-dimensional gel stained with Coomassie. The bottom panel is a two-dimensional immunoblot probed with polyclonal sera against maize cpn60. The positions of mitochondrial HSP70 and cpn60 are indicated by brackets in FIG. 1B.
Figure 2:
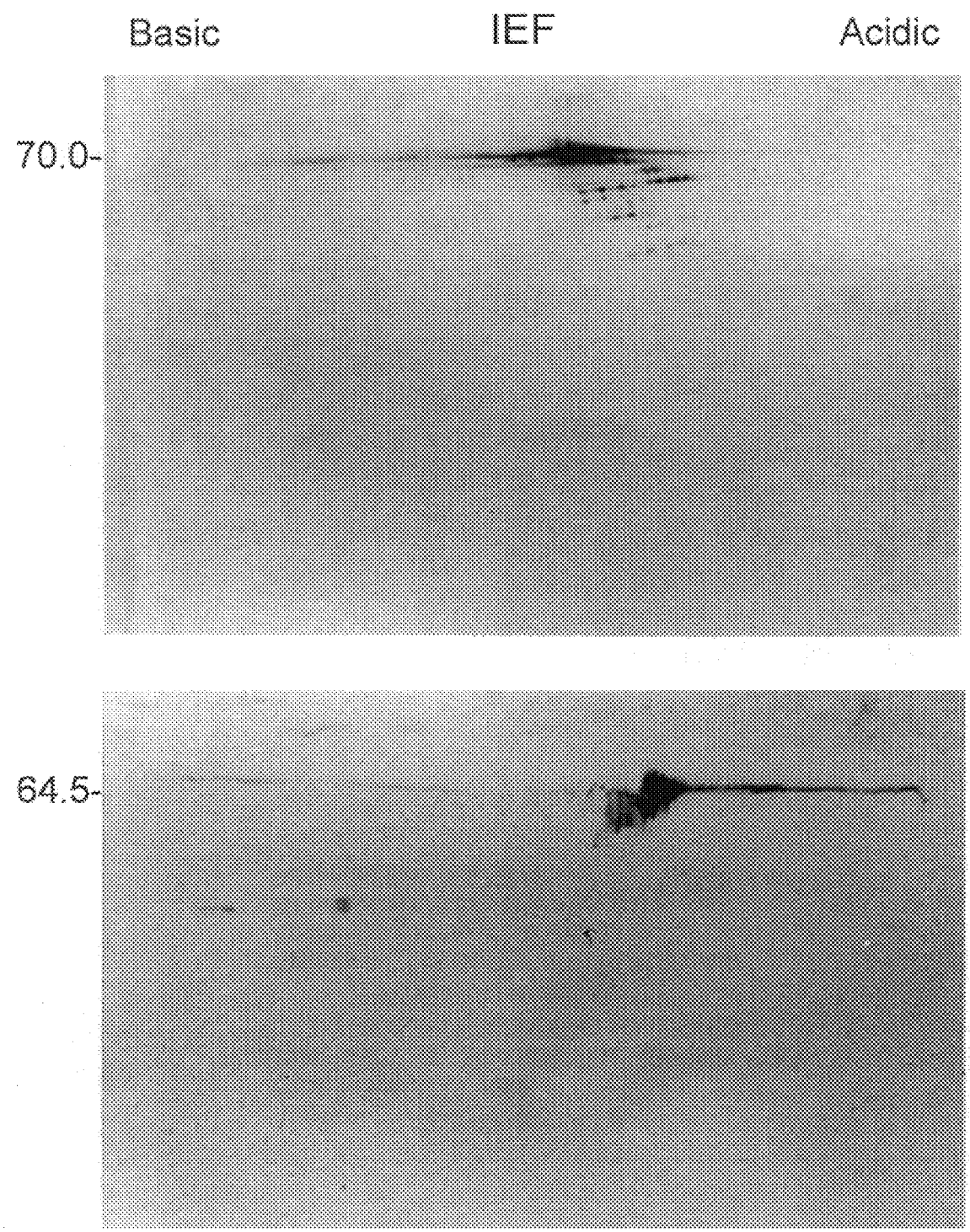
FIG. 2 demonstrates the identification of maize mitochondrial HSP70 and cpn60 monoclonal antibodies (MAbs) with two-dimensional immunoblots. Two-dimensional immunoblots were prepared with approximately 300 μg of maize mitochondrial proteins and probed with MAbs. The top panel was probed with MAb HSP70B and the bottom panel with MAb cpn60A. Approximate molecular masses are indicated to the left (kD)

Heat stress response of maize mitochondria in planta was evaluated. It was found that levels of HSP70 and HSP60 do not change to any significant extent during heat stress treatments. In contrast, levels of mitochondrial HSP22 increase dramatically during stress and decrease after the stress is relieved. HSP22 has been identified as a member of the mitochondrial sHSP superfamily, the first identification of a mitochondrion localized sHSP in a heat tolerant plant. Experiments have indicated that mitochondrial HSP22 is responsible for protecting heat tolerant plants during heat stress.

Methods are disclosed for determining a plant's ability to survive in heat stress conditions by analyzing the level of expression of HSP22 in heat-stressed plants and comparing the amount of expression to a standard or a sample population. This expression can be measured through the use of antibodies (polyclonal, monoclonal, or fragments thereof) or nucleic acid probes that are sufficiently homologous to bind the mRNA encoding HSP22.

Combinations are disclosed for determining a plant's ability to tolerate heat stress conditions. These combinations will include the components necessary to determine a plant's ability to tolerate heat stress conditions. These combinations will incorporate the methods and principles disclosed in the examples listed below.

Nucleic acid molecules presented in this disclosure will enable the creation of full-length nucleic acid molecules encoding maize HSP22 and fragments thereof. Specifically, the disclosed oligonucleotides of SEQ. ID. NOs. 2 and 3, or any other molecules that hybridize to selected portions of SEQ. ID. NO. 7, may be utilized to produce copies of the selected portions of the disclosed nucleic acid molecules which may be utilized for expressing the disclosed protein. Additionally, it is well-known by those of ordinary skill in the art that oligonucleotide design allows an unlimited choice for incorporating restriction endonuclease sites into a vector and a product. The flexibility in oligonucleotide selection and restriction endonuclease site selection allows several choices for the method of preparation of the nucleic acid molecules of the present invention.

It is also well-known to practitioners of the art that the nucleic acid molecules may be recombinant or synthetic or partly synthetic and partly recombinant. Recombinant implies the use of molecular biology tools. Synthetic refers to the use of chemical synthetic procedures.

The present invention includes vectors containing nucleic acid molecules encoding HSP22. For example, the vector could comprise SEQ. ID. NOs. 1, 4, 5, 7, or a nucleic acid molecule encoding SEQ. ID. NO. 6. In one embodiment, the vector includes regulatory molecules operably positioned within the vector, whereby the nucleic acid molecules encoding HSP22 are expressed. These vectors used for expressing a given protein, or a portion thereof, are commonly referred to as expression vectors. Often these expression vectors comprise at least one origin of replication, at least one promoter, at least one ribosome binding site, and at least one terminator. Vectors often contain many other elements known to those of ordinary skill in the art. These vectors can be viral, prokaryotic or eukaryotic in origin and may serve a variety of functions not limited to expression.

The present invention includes cells transformed with various vectors. In one embodiment, this cell is an *E. coli* cell of the appropriate genetic makeup, transformed with an expression vector of the present invention and is capable of expressing HSP22. Such cells, commonly known as host cells, can be either prokaryotic or eukaryotic. It is understood by those of ordinary skill in the art that a recombinant molecule containing the nucleic acid sequence of the present invention can be used to transform a variety of hosts using any known technique for transformation. Additionally, there are other methods besides transformation for the introduction of nucleic acids into host cells. These methods include, but are not limited to, transvection and direct introduction of nucleic acid molecules.

Vectors transformed with the nucleic acid molecules of the present invention may also be utilized to transform plant cells to form plants that have the ability to better survive in heat stress conditions. Specifically, a plant species modified to express an amount of HSP22 in excess of a naturally occurring amount of HSP22.

In addition to the nucleic acid molecules, vectors, and transformed cells, the present invention further includes a method for the production of HSP22. This method involves the insertion of a nucleic acid molecule that encodes HSP22 into an expression vector. This vector is transformed into an appropriate host bacterial cell so that the nucleic acid molecules encoding HSP22 may be expressed. The HSP22 is then isolated from the bacteria through protein purification techniques. Through this process, HSP22 can be produced in large quantities for use in industry and research. Additionally, it is known to those skilled in the art that there are several methods besides transformation with expression vectors that allow the expression of protein from a given nucleic acid molecule. One example is transvection of certain host cells with mRNA. In another example, expression may be achieved from a nucleic acid molecule in vitro rather than in vivo.

The present invention further includes a product of the above discussed method. This product is isolated HSP22.

The present invention includes isolated nucleic acid molecules that encode for HSP22. The procedures listed below may be implemented to produce large quantities of the disclosed nucleic acid molecules. Additionally, these molecules can be produced through synthetic or recombinant means. These procedures allow the industrial and scientific community access to the nucleic acid molecule of the present invention for further studies or for the purpose of expression in order to produce and isolate HSP22.

An antibody for HSP22 is disclosed. The antibody can be polyclonal, monoclonal, or a fragment thereof. Additionally a hybridoma producing functional monoclonal antibodies for HSP22 is disclosed.

The following discussion will assist in defining the structure for a portion of the claimed invention. The genetic code is degenerate. This means that several combinations of three nucleotides will code for the same amino acid. For example, Leu can be coded for by 6 combinations of 3 nucleotides. Many nucleic acid molecules can code for a particular amino acid molecule. Thus, there is a multitude of nucleic acid molecules that could code for the sequences of the present invention. It is intended that those nucleic acid molecules that both hybridize under stringent conditions with the nucleic acid molecule of the present invention and that code for a peptide having substantially the same physical characteristics as HSP22 are included within the scope of this invention.

Stringent conditions are defined as hybridization in a medium containing 6×SSC or 6×SSPE and 40% formamide at a temperature of 37° C. and a wash at 37° C. with 2×SSC or 2×SSPE containing 0.1% SDS. These solutions can be prepared from 20× SSC or SSPE which comprise the following compositions. The 20× SSC is formed by mixing 175.3 g of sodium chloride and 88.2 g of sodium citrate in 1 L of water with a final pH of 7.0. The 20× SSPE is formed by mixing 210 g of sodium chloride, 27.6 g $NaH_2 PO_4 H_2O$, and 40 μl of 0.5 MEDTA in 1 L of water. Any nuclei acid molecules that hybridize to SEQ. ID. NO. 7 in a solution containing 6×SSC or 6×SSPE and 40% formamide at 37° C. and remains bound to SEQ. ID. NO. 7 when the milieu is changed to 2×SSC or 2×SSPE containing 0.1% SDS are those nucleic acid molecules defined as hybridizing under stringent conditions. Additionally, it is well known in the art that several factors affect hybridization including the length and nature of the probe, nature of the target, concentrations of salts, components in the hybridization solution, and temperature. Therefore, this description of stringency includes equivalent hybridization and wash conditions. The results of the hybridization can be easily determined by one skilled in the art through Southern blot analysis.

In describing the nucleic acid molecules of the present invention, both structure and function or physical characteristics are utilized. The structure is provided by the above description of stringency; those nucleic acid molecules that hybridize under stringent conditions. The function or physical characteristics are provided by the following discussion of the physical characteristics of HSP22. Therefore, those nucleic acid molecules that hybridize to SEQ. ID. NO. 7 and whose protein products have physical characteristics substantially similar to HSP22 are included within the scope of the present invention. Additionally, those nucleic acid molecules that hybridize to SEQ. ID. NO. 7 and whose protein products have physical characteristics substantially similar to HSP22 may code for peptide fragments which are also included within the scope of the present invention.

Those of ordinary skill in the art will recognize that methods for vector construction and protein expression provided in the following examples are the preferred embodiment and that there are other techniques, vectors, and cell lines that could be implemented for constructing and expressing proteins or fragments thereof in either procaryotic or eukaryotic systems. The preferred embodiment disclosed herein does not limit the scope of the invention. There are a variety of alternative techniques and procedures available to those with ordinary skill in the art that would permit one to perform modifications on the present invention. It is also well-known in the art that commercially available kits allow the modification and incorporation of the present invention. It is further recognized that those with ordinary skill in the art could employ any of a number of known techniques to modify the nucleic acid molecules of the present invention, in vitro or in vivo, and develop them further by established protocols for gene transfer and expression.

IDENTIFICATION OF MITOCHONDRIAL HSP22

Figure 3:
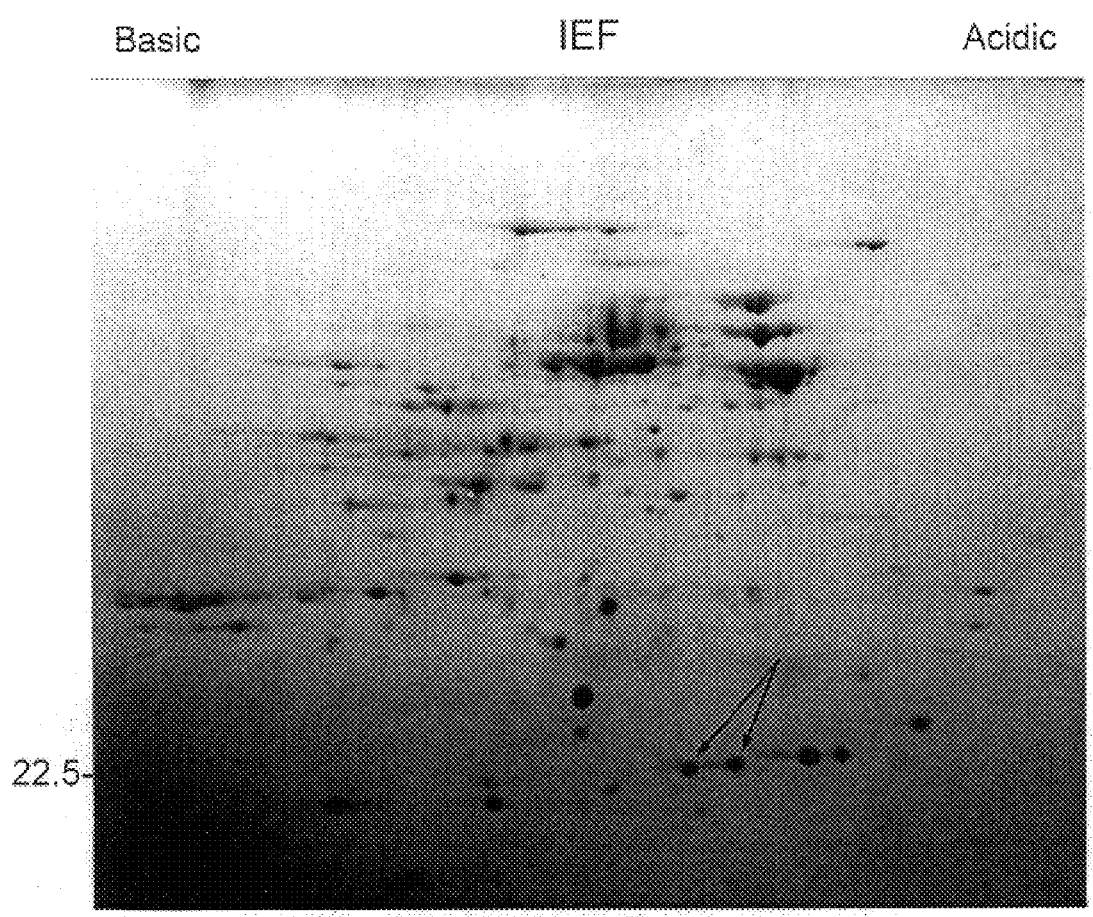
FIG. 3 is a two-dimensional Coomassie-stained gel of heat-shocked seedling mitochondrial proteins. Three-day-old etiolated maize seedlings grown at 29° C. were heat-shocked for four hours at 42° C. and the mitochondria isolated. Three hundred micrograms of mitochondrial protein were run on a two-dimensional gel and stained with Coomassie blue. The two spots that are indicated by arrows are HSP22A (acidic) and HSP22B (basic). HSP22 protein approximate molecular mass is indicated to the left (kD)

Experiments have been conducted to evaluate the expression of mitochondrial proteins of maize during conditions of heat stress. Mitochondria were isolated from three-day-old etiolated shoots grown at 29° C. Three hundered μg of the mitochondrial protein was analyzed on two-dimensional SDS-PAGE gels stained with Coomassie Brilliant Blue, as seen in FIG. 1B. These methods are disclosed in Example I. The designated protein spots in FIG. 1B correspond to plant mitochondrial HSP70 and chaperonin 60 (cpn60). FIG. 3 is of mitochondria isolated from similar seedlings, except these seedlings were treated with a four-hour heat shock at 42° C. Analysis of these Coomassie-stained gels indicates that very few protein spots increased in intensity during heat stress, including the HSP70 and cpn60 proteins. However, visual inspection of the gel in FIG. 3 demonstrates that two protein spots were significantly increased when compared to a non-heat-shocked gel. The two protein spots that demonstrate the increase have apparent molecular weights of approximately 22 kDa. This demonstrates that one response to heat stress in a heat tolerant mitochondria is an increase in the level of this 22 kDa protein. These protein spots have been designated as HSP22.

PRODUCTION OF ANTIBODIES TO MITOCHONDRIAL HSP22

Figure 4:
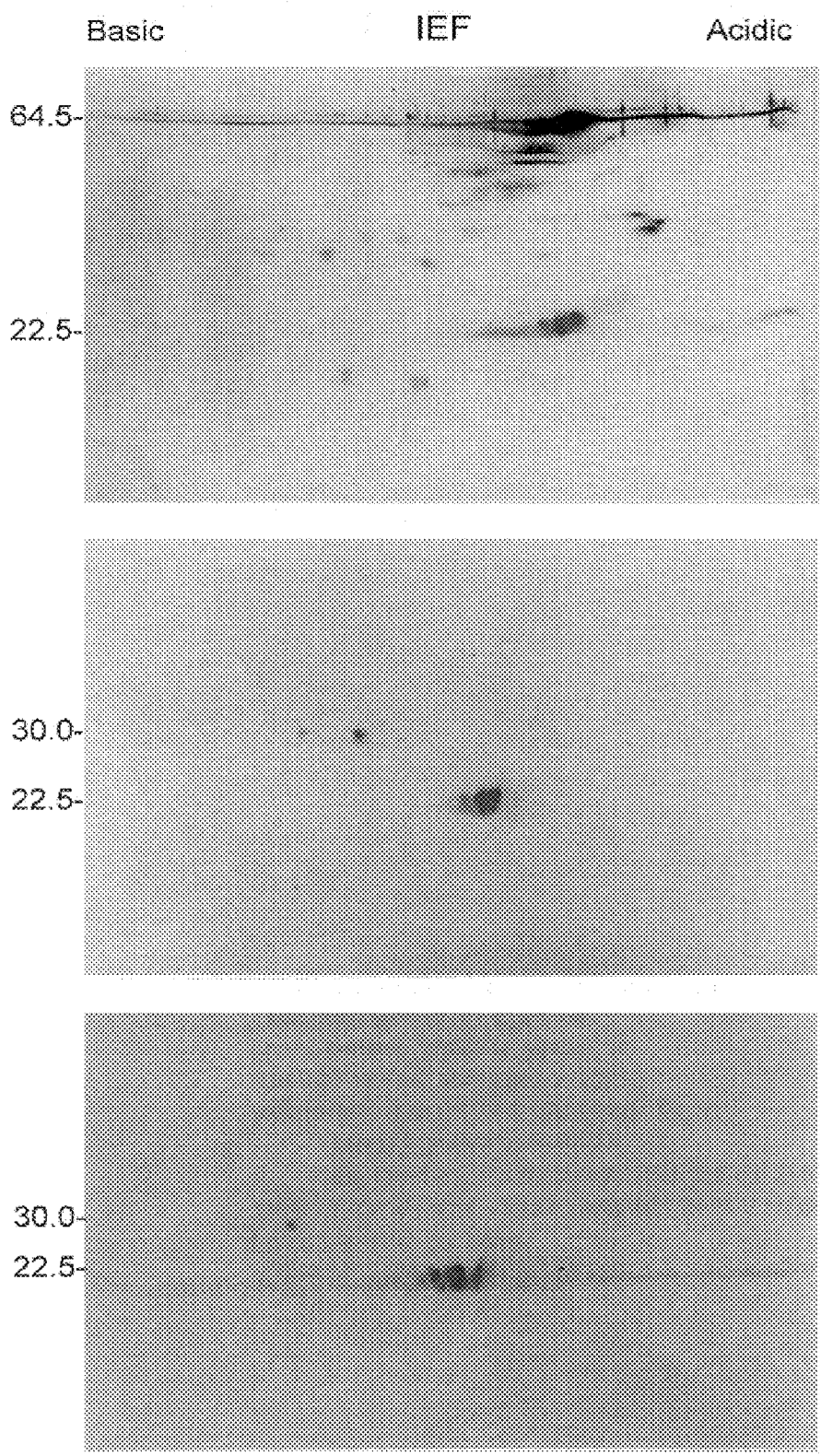
FIG. 4 illustrates mitochondrial HSP22 polyclonal antibodies, affinity purified polyclonal antibodies, and monoclonal antibody, respectively. The top panel is a two-dimensional immunoblot of heat-shocked maize mitochondrial proteins probed with polyclonal antisera to HSP22. A similar unprobed blot was stained with Ponceau S to reveal the proteins, the spots corresponding to HSP22 were cut out, destained, incubated with the HSP22 polyclonal antisera, and the antibodies eluted with a low pH wash. The middle panel is a two-dimensional immunoblot probed with these affinity purified polyclonal antibodies. The bottom panel is a similar two-dimensional immunoblot probed with the monoclonal antibody generated to the HSP22 proteins.

The antibody production was accomplished by injecting mice independently with one of the two HSP22 protein spots from the two-dimensional SDS-PAGE gels from the heat-shocked maize mitochondria. The upper panel of FIG. 4 illustrates a two-dimensional western blot of heat shock mitochondrial proteins probed with the polyclonal sera. On several occasions, the polyclonal antibodies were not specific to HSP22 and also bound to cpn60.

Polyclonal antibodies specific to the HSP22 spots were affinity purified using HSP22 protein blots. The specificity of these affinity purified antibodies is demonstrated in the western blot of heat shock mitochondria at the middle panel of FIG. 4. These mice were eventually sacrificed for the production of monoclonal antibodies. After three fusions, a monoclonal antibody was obtained that was specific for HSP22. The specificity of this monoclonal antibody is shown in the western blot of heat shock mitochondria at the lower panel of FIG. 4. The polyclonal and monoclonal antibodies for maize HSP22 were found to bind to minor proteins of about 30 kDa. These are most likely precursor forms of HSP22.

In addition to the monoclonal antibodies, fragments were generated using immobilized papain and immobilized pepsin as described by Pierce Chemical Company, Rockford, Ill., which is hereby incorporated by reference. Methods for the production of the antibodies and fragments thereof are disclosed in Example II.

CHARACTERIZATION OF MITOCHONDRIAL HSP22

Figure 5:
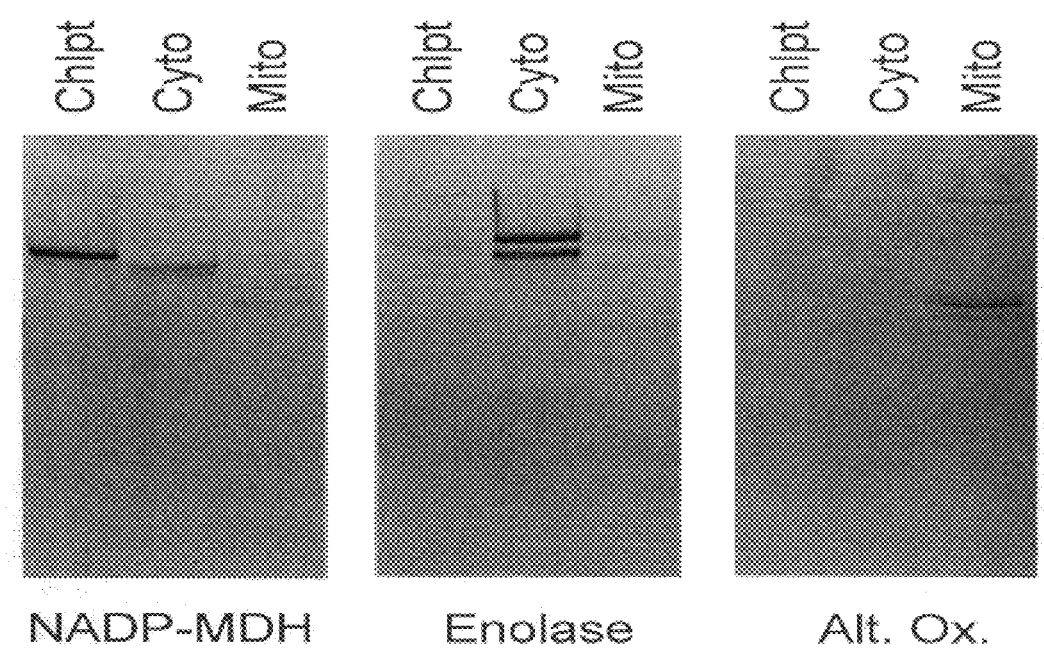
FIG. 5 illustrates distinct subcellular fractions from maize seedlings. Immunoblots were prepared from the chloroplastic, cytosolic, and mitochondrial fractions (20 μg per lane) and probed with antibodies to known marker enzymes. The chloroplast (Chlpt) proteins were isolated from two-week-old maize seedlings. The cytoplasmic (Cyto) and mitochondrial (Mito) fractions were isolated from three-day-old etiolated shoots grown at 29° C. The chloroplast marker is the 45 kD NADP-malate dehydrogenase protein (NADP-MDH); the cytoplasm marker is the 50 and 52 kD enolase proteins; and the 35 and 36 kD proteins of the alternative oxidase (Alt. Ox.) represent the mitochondrial marker.
Figure 6:
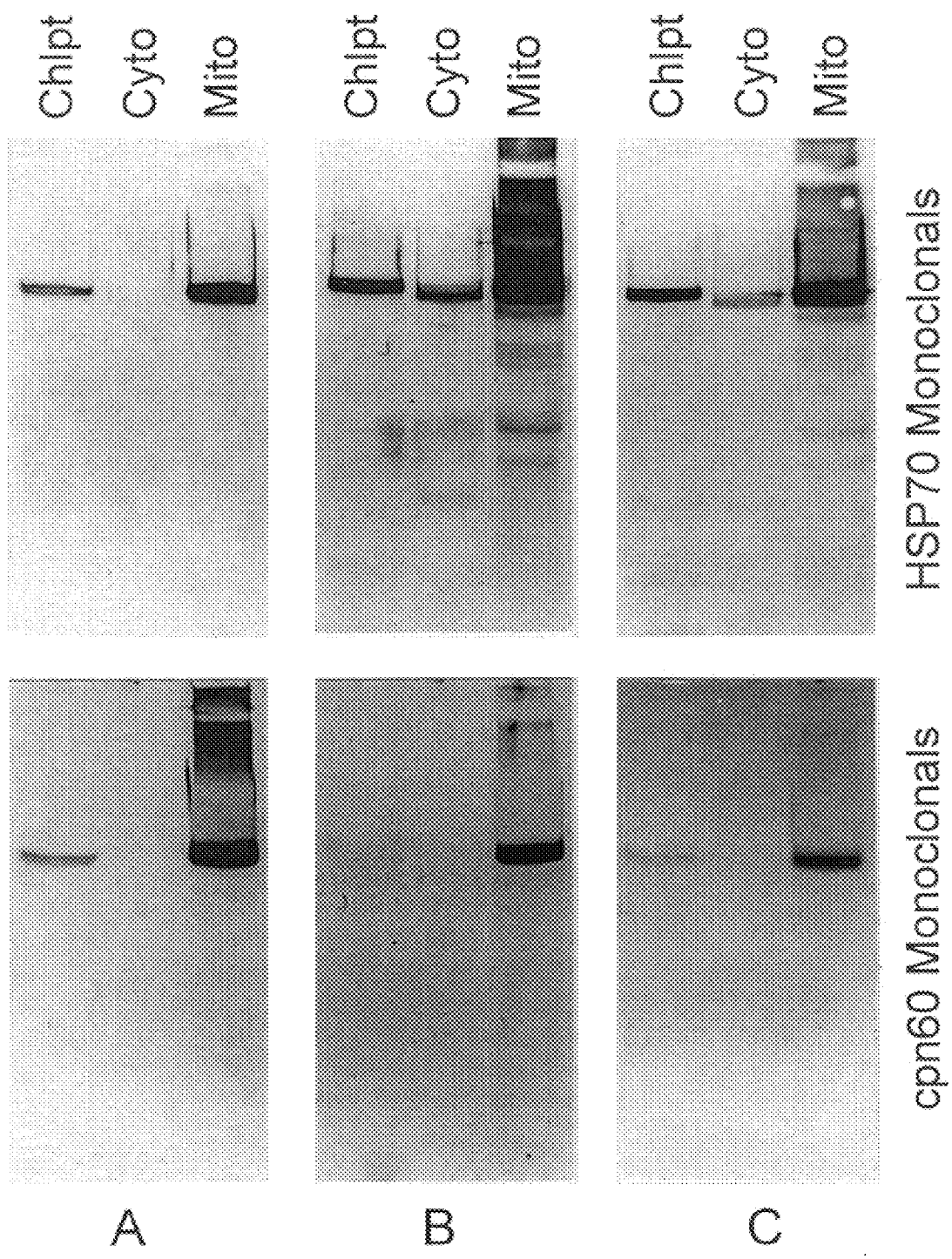
FIG. 6 illustrates HSP70 and cpn60 monoclonal antibody cross-reactivity to different subcellular fractions of maize. Immunoblots similar to those in FIG. 5 were prepared and probed with the MAbs to HSP70 and cpn60. The top panels illustrate blots probed with MAbs HSP70A, HSP70B, and HSP70C which identify the 70 kD species. The bottom panels illustrate blots probed with cpn60A, cpn60B, and cpn60C which identify a 64.5 kD species.

Experiments were performed to determine if the monoclonal antibodies to HSP22 would recognize homologs in the chloroplast and cytoplasmic subcellular fractions. Chloroplasts, cytoplasm, and mitochondria were isolated and the distinctness of the fractions was evaluated using immunoblots and antibodies to marker enzymes (FIG. 5). The cytoplasm and mitochondrial fractions were from three-day-old etiolated shoots, while the chloroplast fraction was from ten-day-old light grown seedlings. NADP-malate dehydrogenase was used as a marker for the chloroplast stroma (Edwards and Huber, 1981), enolase as a maize cytoplasmic marker (Lal et al., 1994), and the alternative oxidase as a mitochondrial marker (Elthon et al., 1989). FIG. 5 demonstrates that the subcellular fractions were indeed distinct.

Figure 7:
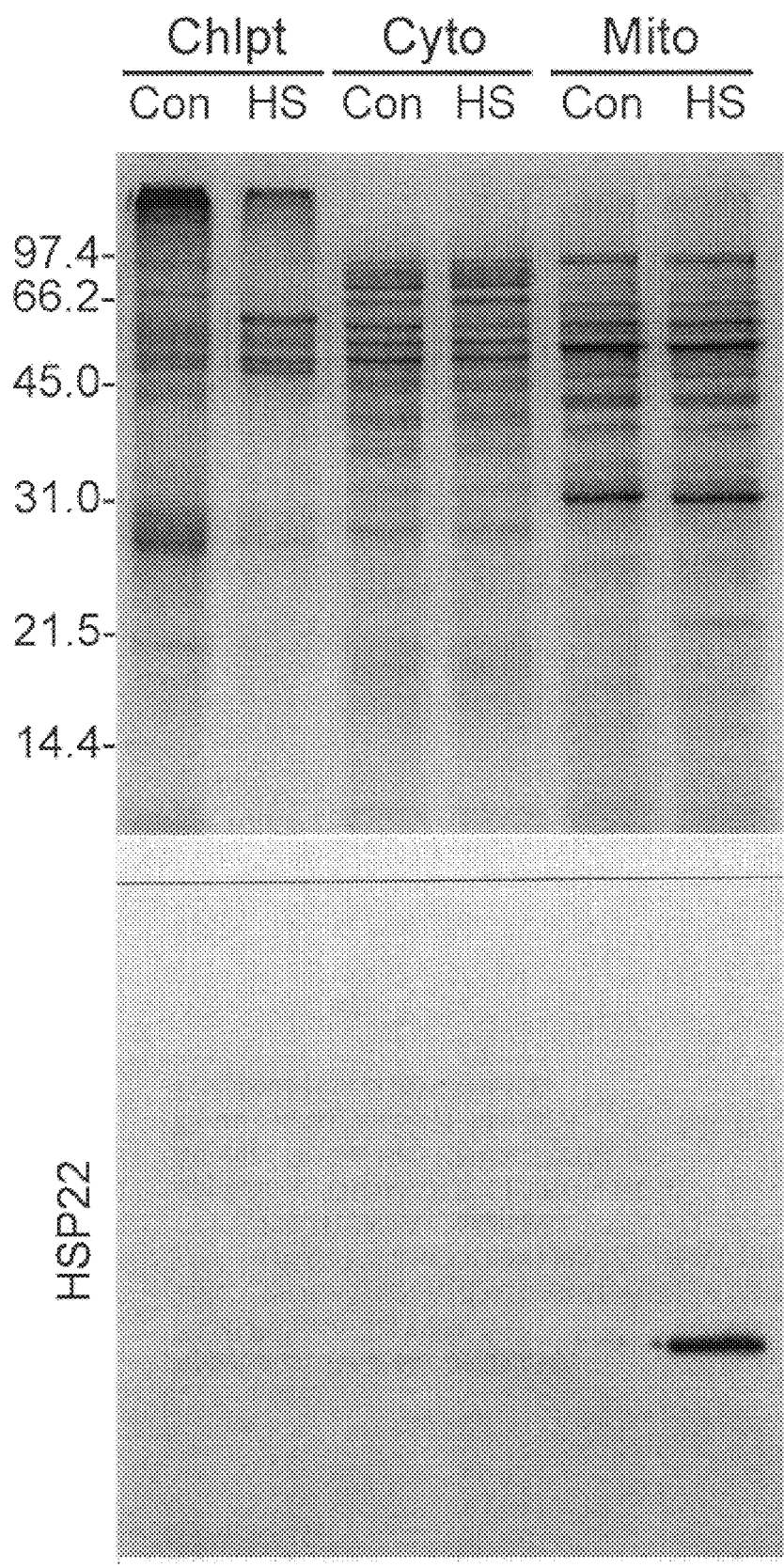
FIG. 7 illustrates subcellular cross-reactivity of the HSP22 monoclonal antibody. The top panel is a Coomassie-stained SDS-PAGE gel of subcellular fractions (20 μg per lane) isolated from heat-shocked and control maize tissue. The chloroplast (Chlpt) proteins were isolated from two-week-old maize seedlings treated for four hours at 42° C. in the dark (HS) or left at the 21° C. growth temperature (Con). The cytoplasmic (Cyto) and mitochondrial (Mito) fractions were isolated from three-day-old etiolated shoots grown at 29° C. (Con) and heat-shocked for four hours at 42° C. (HS). The bottom panel is an immunoblot of a similar gel probed with the monoclonal antibody to HSP22. Approximate molecular mass markers are indicated to the left (kD)

Control and 42° C. heat-shocked seedlings were fractionated into chloroplast, cytoplasm and mitochondrial fractions and then probed with the HSP22 monoclonal antibody. The upper panel of FIG. 7 is a Coomassie-stained gel of the cellular fractions. The lower panel is an immunoblot probed with the HSP22 monoclonal. These results indicate that the monoclonal is specific to the mitochondrial fraction. Methods for the determination of homolog recognition of proteins in subcellular fractions by HSP22 monoclonal antibodies is disclosed generally in Examples I and II.

Submitochondrial distribution of HSP70, cpn60, and HSP22 was determined through the following: Mitochondria from control and heat-shocked seedlings were subfractionated into membrane, soluble, and complex fractions. Immunoblots of the fractions from control and heat shock mitochondria were run and probed with the monoclonals to HSP70, cpn60, and HSP22. The results indicated that the heat shock treatment had no effect on the distribution of HSP70 and cpn60. HSP70 was found primarily in the soluble fraction, cpn60 was most prevalent in the complex fraction, and HSP22 was found primarily in the soluble fraction.

Figure 8:
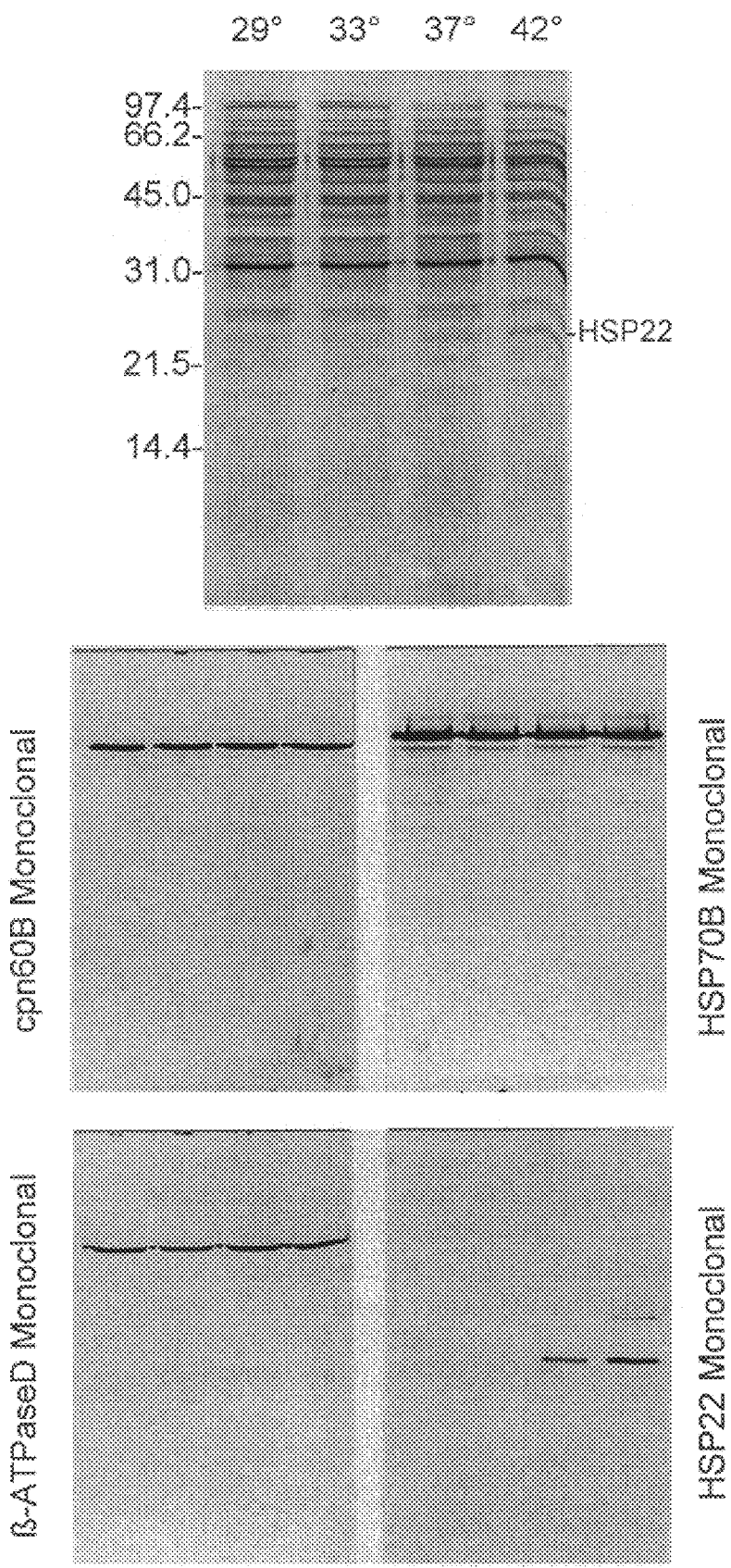
FIG. 8 illustrates the effect of temperature on the induction of mitochondrial cpn60, HSP70 and HSP22 proteins. Three-day-old etiolated maize seedlings were treated for four hours at either 29° C. (control), 33° C., 37° C., or 42° C. The mitochondria were isolated and analyzed by SDS-PAGE and immunoblots. The top panel is a Coomassie stained SDS-PAGE gel loaded with 20 μg of mitochondrial protein per lane. Approximate molecular mass markers are on the left (kD). The four other panels are immunoblots of similar gels probed with the cpn60B monoclonal (center left), the HSP70B monoclonal (center right), the β-ATPase D monoclonal as a control (bottom left), and the HSP22 monoclonal (bottom right)

Experiments were done to determine the temperature necessary for HSP22 to appear in maize mitochondria. To accomplish this, etiolated shoots were subjected to three different heat shock treatments. After the four-hour heat shock at the respective temperatures, the mitochondria were isolated. The upper panel of FIG. 8 depicts a Coomassie-stained SDS-PAGE gel loaded with 20 $\mu$g of mitochondrial protein per lane. The four-hour heat-shock treatments were done at 29° C. (control), 33° C., 37° C., and 42° C. The remaining panels in FIG. 8 illustrate western blots of gels similar to Coomassie-stained SDS-PAGE gels probed with cpn60 monoclonal (mid left), HSP70B monoclonal (mid right), β-ATPase D monoclonal (lower left), and HSP22 monoclonal (lower right). These gels demonstrate that cpn60, HSP70, and the β-ATPase subunit proteins are not significantly affected by the heat shock treatments, whereas the HSP22 protein expression begins somewhere above 33° C. It appears from the gel that the quantity of HSP22 present at 37° C. is significantly less than at 42° C. These experiments indicate that at some point between 33° C. and 37° C. expression of HSP22 begins, and further, that the expression increases between 37° C. and 42° C.

Figure 9:
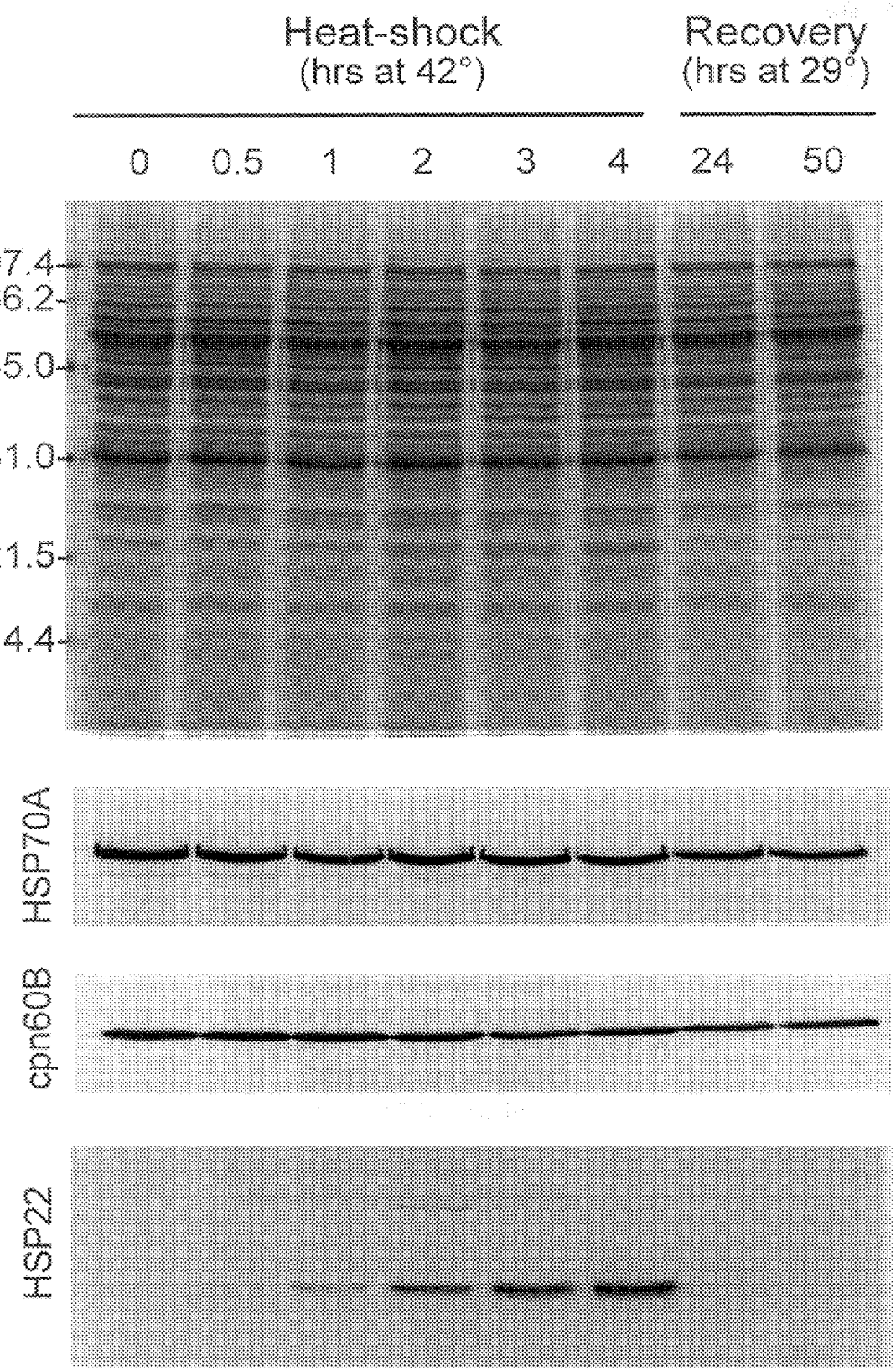
FIG. 9 illustrates SDS-PAGE and immunoblot analysis of the time course of induction for maize mitochondrial HSP70, cpn60, and HSP22 proteins. Three-day-old etiolated maize seedlings grown at 29° C. were placed at 42° C. (0 hours at 42° C.) and samples were removed after 0.5, 1, 2, 3, and 4 hours of heat shock, and the mitochondria were immediately isolated. Seedlings that received four hours of heat shock were returned to the 29° C. incubator and allowed to recover for 24 or 50 hours prior to mitochondrial isolation. The top panel is a Coomassie-stained SDS-PAGE gel loaded with 20 μg of mitochondrial protein per lane. Approximate molecular mass markers are on the left (kD). The three bottom panels are immunoblots of similar gels probed with the MAbs HSP70A, cpn60B and HSP22.

Experiments were performed to determine the decay time for HSP22. Three-day-old etiolated maize shoots were placed at 42° C. and samples were removed at various time intervals. The mitochondria of these interval samples were then isolated. After the heat-shock treatment, two samples were returned to the 29° C. incubator and allowed to recover for 24 and 50 hours. The upper panel of FIG. 9 illustrates a Coomassie-stained SDS-PAGE gel loaded with 20 $\mu$g of mitochondrial protein per lane. The two middle panels of FIG. 9 illustrate western blots of similar SDS-PAGE gels probed with the monoclonal antibodies HSP70B and cpn60B. The bottom panel of FIG. 9 is a western blot probed with the HSP22 monoclonal antibody. These experiments demonstrate that HSP22 protein begins to appear about one hour after the onset of the heat shock and continues to increase steadily to four hours. These experiments further demonstrate that neither HSP70 nor cpn60 change their expression when exposed to heat shock. In addition to the increased expression of HSP22, essentially all of the HSP22 is degraded after relief of the heat stress for 24 hours. Both the increased expression after exposure to heat shock and the degradation after relief of heat shock indicate that HSP22 expression and degradation are related to the timing of heat shock.

Figure 10:
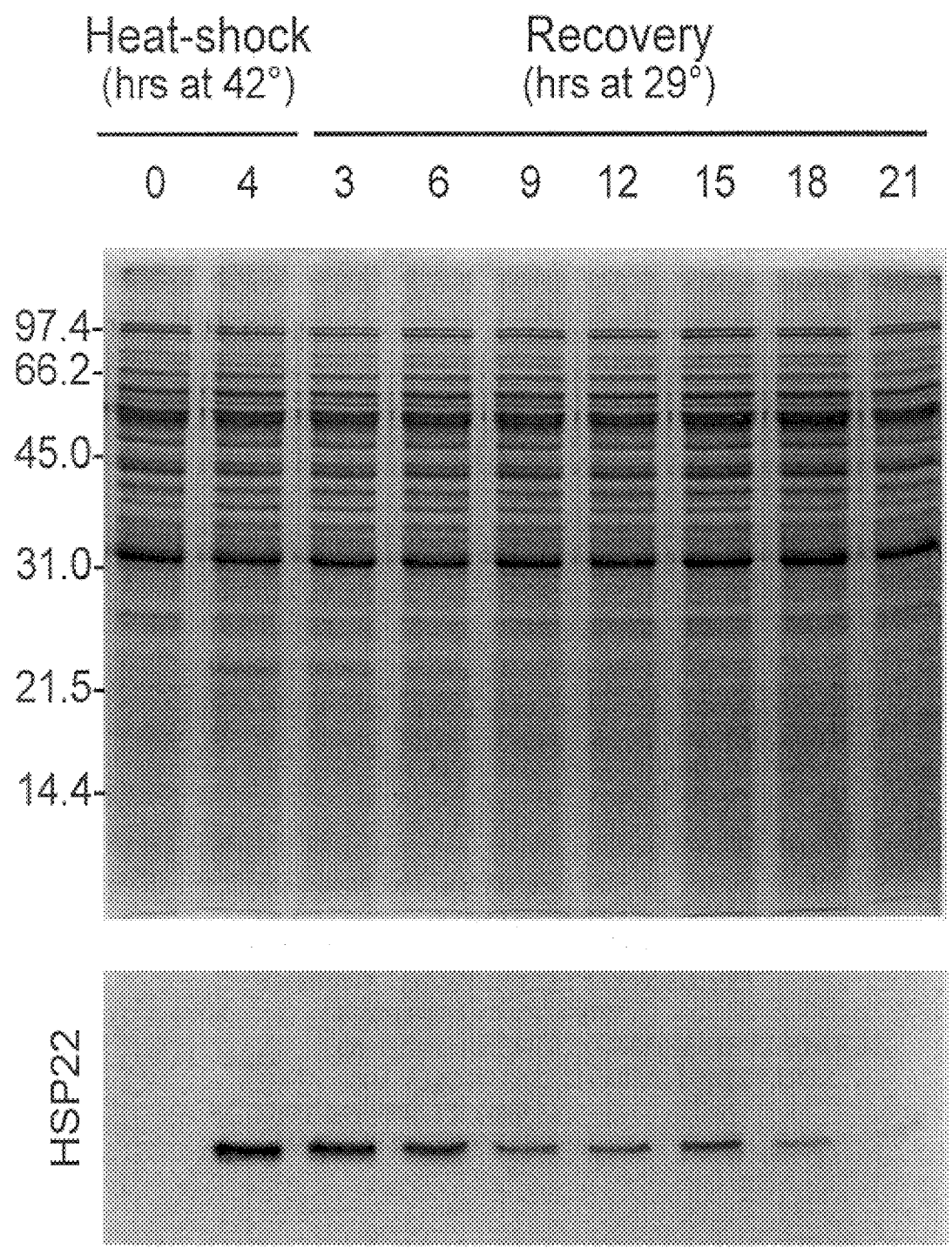
FIG. 10 illustrates SDS-PAGE and immunoblot analysis of the time course of HSP22 decay from heat-shocked maize mitochondria. Three-day-old etiolated maize seedlings were grown at 29° C. and heat shocked at 42° C. for four hours and then returned to 29° C. to recover for 3, 6, 9, 12, 15, 18, or 21 hours. Mitochondria were isolated from samples taken just prior to and following heat-shock (0 and 4 hours at 42° C.) and immediately after the above recovery times. The top panel is a Coomassie-stained SDS-PAGE gel loaded with 20 μg of the mitochondrial isolations per lane. Approximate molecular mass markers are on the left (kD). The bottom panel is an immunoblot of a similar gel probed with the HSP22 MAb.
Figure 11:
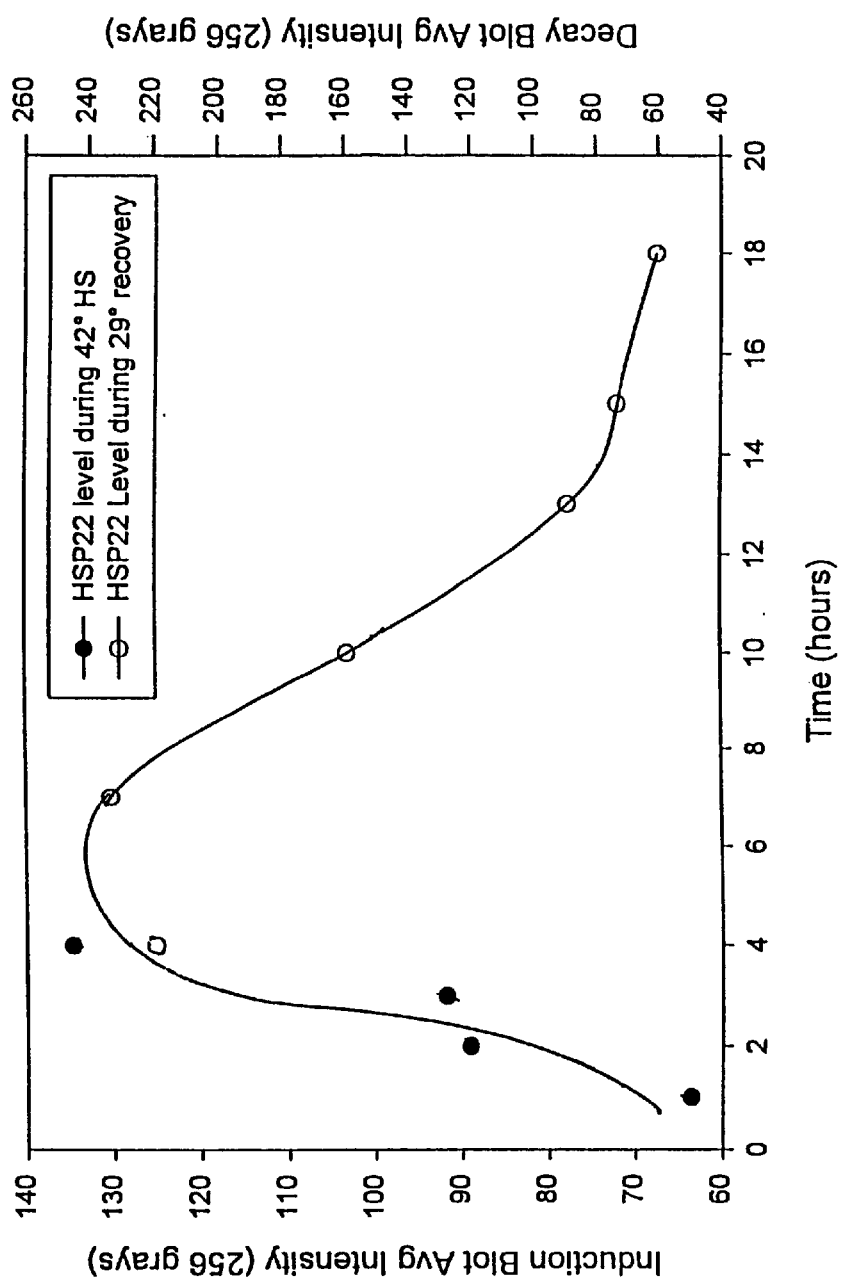
FIG. 11 illustrates the induction and decay of HSP22 in the mitochondrial fraction of B73 maize etiolated shoot mesocotyls during heat shock and recovery. Analysis of this graph demonstrated that the half life of HSP22 protein is about four hours.
Figure 12:
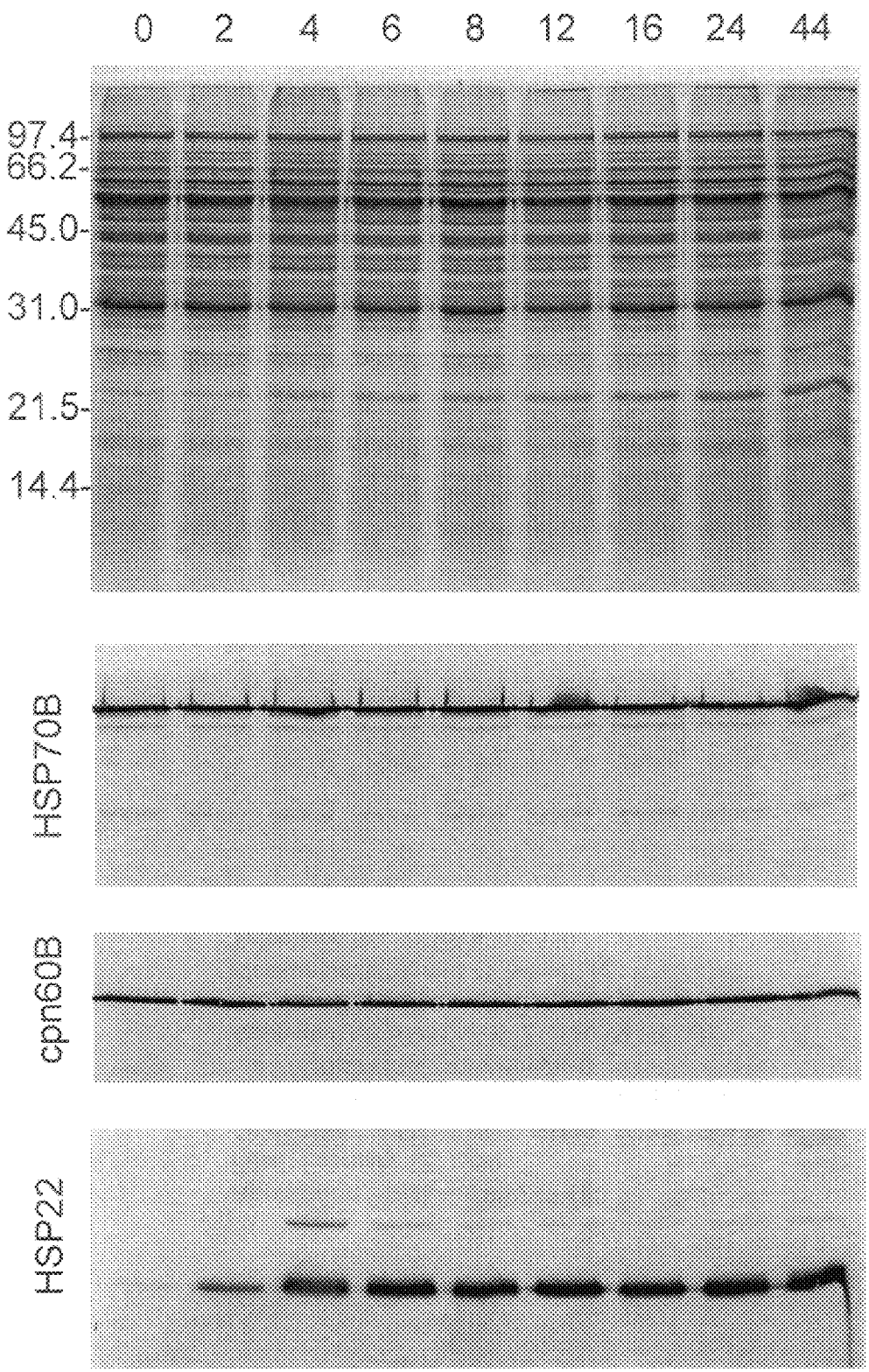
FIG. 12 illustrates SDS-PAGE and immunoblot analysis of the effect that continuous heat shock has on the levels of maize mitochondrial HSP70, cpn60, and HSP22 proteins. Three day-old etiolated maize seedlings grown at 29° C. were placed at 42° C. Samples were removed after 0, 2, 4, 6, 8, 12, 16, 24, and 44 hours of heat shock. The mitochondria were immediately isolated. The top panel illustrates a Coomassie-stained SDS-PAGE gel loaded with 20 μg of mitochondrial protein per lane. Approximate molecular mass markers are on the left (kD). The three bottom panels are immunoblots of similar gels probed with the MAbs HSP70B, cpn60B and HSP22, respectively.
Figure 13:
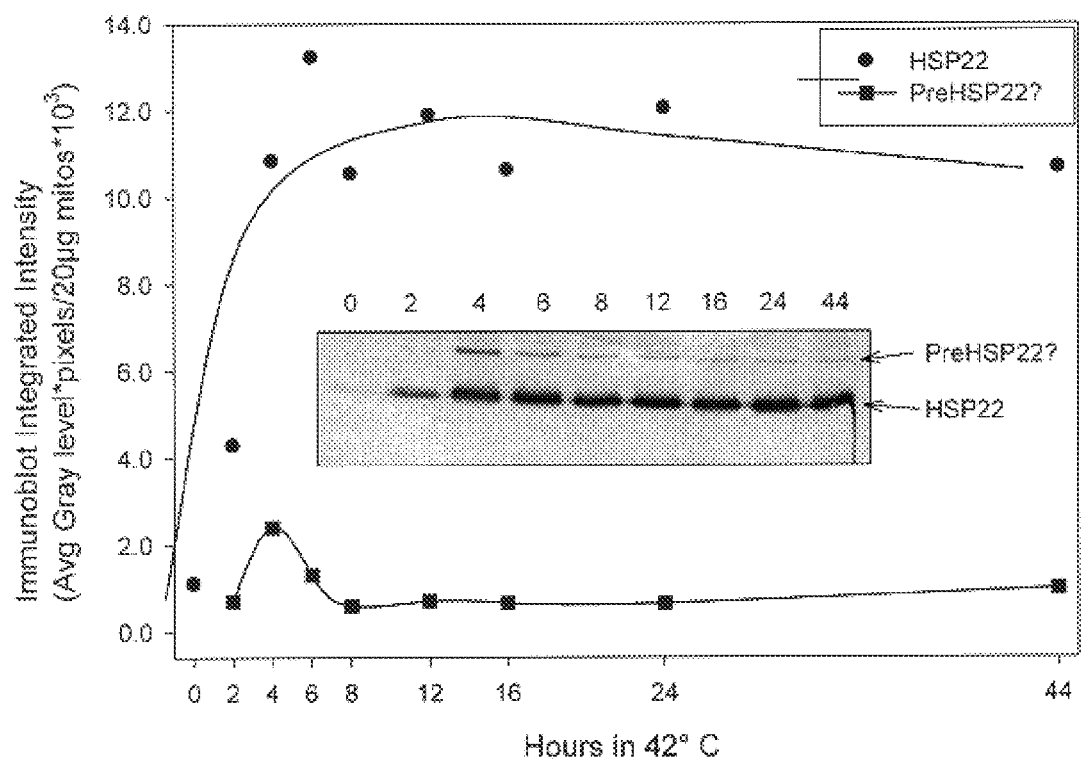
FIG. 13 illustrates a graph of the induction of HSP22 in three-day-old B73 maize mesocotyls under continuous heat shock. These results were obtained by quantitating the areas from the SDS-PAGE and immunoblot analysis of continuous heat shock of maize mitochondria at 0, 2, 4, 6, 8, 12, 16, 24 and 44 hours as seen in FIG. 12. The graph demonstrates that after maximal induction, the levels remained high until the experiment was terminated at 44 hours of heat shock. Additionally, the graph illustrates a 30 kDa band that is believed to be a precursor form of HSP22.

These initial experiments were further refined to better characterize the induction and decay of mitochondrial HSP22. This was accomplished by taking samples at various times after the relief of heat stress. The results are illustrated in FIG. 10 and indicate that HSP22 levels drop gradually, but are essentially absent at 21 hours. The areas on the induction and recovery blots were quantitated and a half life for HSP22 was calculated. The half life was found to be about four hours (FIG. 11). Additionally, levels of HSP22 expression were further evaluated under a continuous heat shock for various time intervals, as indicated in the upper panel of FIG. 12. This upper panel is a Coomassie-stained gel of mitochondria isolated at various time intervals. The lower three panels are immunoblots probed individually with the monoclonals HSP70B, cpn60B, and HSP22. This illustrates that two hours of heat shock yields significant induction of HSP22 expression, with maximum expression occurring between four and six hours. After maximal induction, the levels remained high until the experiment was terminated after 44 hours of heat shock. The levels of HSP22 were quantitated at the different time intervals and the resulting graph is illustrated in FIG. 13. The 30 kDa band, which is believed to be a precursor form of HSP22, was included in the calculation. Methods utilized for the determination of expression and degradation of HSP22 are disclosed generally in Examples I and II.

These characterization studies demonstrate that the monoclonal antibody is useful in tracking HSP22 expression during the induction and relief of heat stress. Thus, the monoclonal antibody to HSP22 can be used to evaluate the ability to tolerate heat stress in plants by determining the amount of HSP22 expression.

Figure 14:
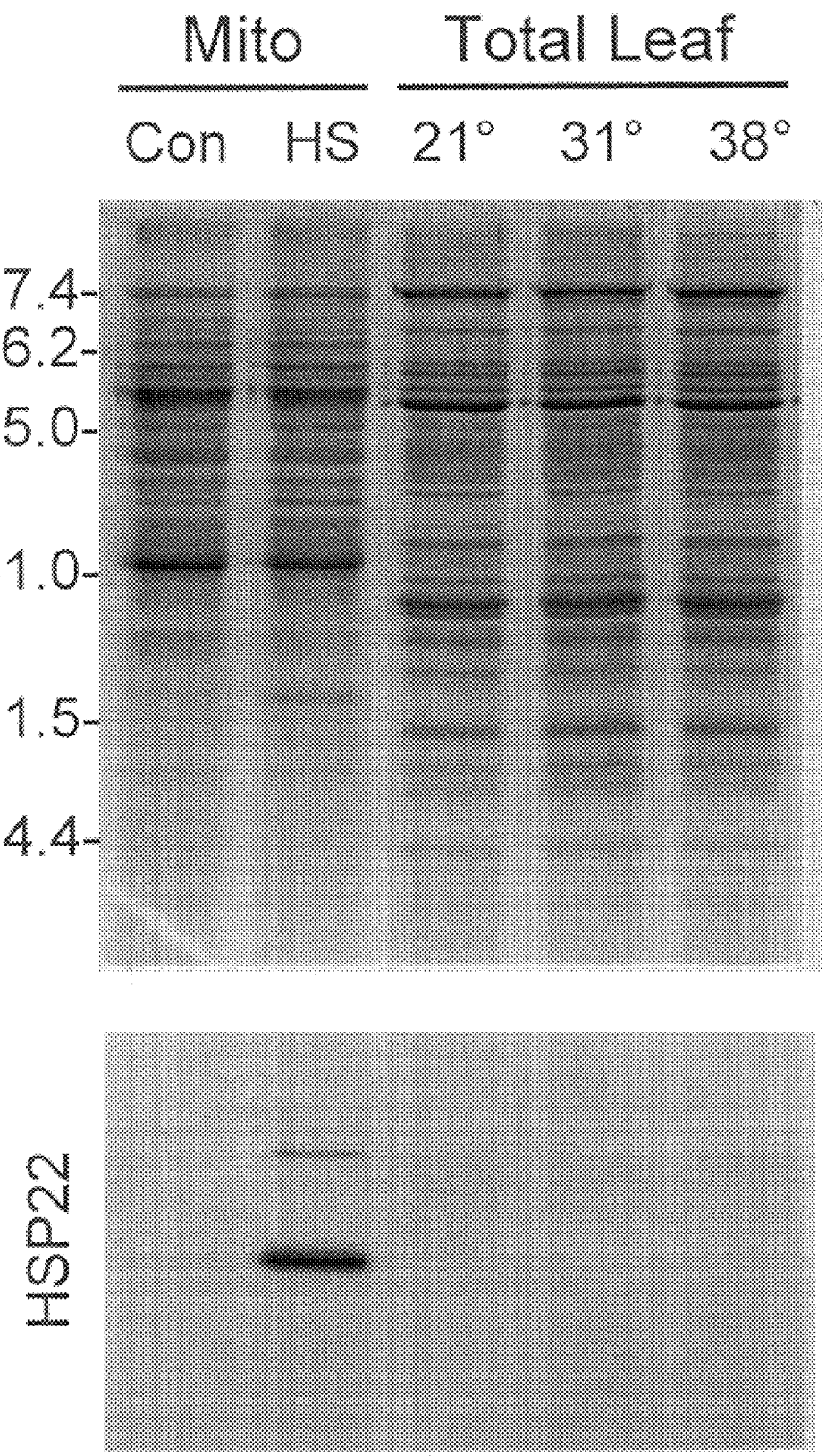
FIG. 14 illustrates a SDS-PAGE and immunoblot analysis of HSP22 levels in protein extracts of whole leaves. The top panel is a Coomassie-stained SDS-PAGE gel loaded with mitochondrial isolations from control and heat shock and total leaf extracts from leaves of ten-day-old light grown maize seedlings at various heat shock temperatures. The bottom panel illustrates an immunoblot of a similar gel probed with the HSP22 MAb. As shown, the HSP22 MAb is able to detect mitochondrial HSP22 in whole leaf extracts of 38° C. heat-stressed seedlings.

Experiments were done to determine if the monoclonal antibody was useful in evaluating HSP22 levels in protein extracts from whole maize leaves. This was tested using maize seedlings grown at 21° C. and then heat shocked for four hours at either 31° C. or 38° C. FIG. 14 illustrates the results from the whole leaf experiments. The upper panel of FIG. 14 is a Coomassie-stained gel of both mitochondrial and whole leaf fractions. The left two lanes are mitochondria isolated from control and heat shocked (42° C. for four hours) etiolated maize shoots and the right three lanes are of proteins extracted from leaves of ten-day-old light grown maize seedlings grown at 21° C. The first whole leaf lane is a control, the second whole leaf lane was heat shocked for four hours at 31° C., and the third whole leaf lane was heat shocked for four hours at 38° C. The lower panel of FIG. 14 is an immunoblot of a gel similar to the upper gel probed with the HSP22 antibody. The results clearly demonstrate that mitochondrial HSP22 was detectable in whole leaf extracts of 38° C. heat-stressed seedlings by the monoclonal antibody to HSP22. This demonstrates that the monoclonal antibody to HSP22 is useful in evaluating the ability to tolerate heat stress by testing whole leaf extracts. Further, it was found that fab and f(ab')$_2$ antibody fragments show greater specificity and have better access characteristics in certain types of assays such as immuno detection in whole tissues.

Additionally, this test can be used to determine a plant's ability to tolerate heat stress by the level of expression of HSP22. The level of expression can be compared to a large sample population or to a known sample to determine if the particular plant has the ability to tolerate heat stress. Those plants with the highest level of HSP22 expression will best tolerate heat stress due to the chaperone qualities of HSP22. Methods for the detection of HSP22 expression in whole leaf samples are disclosed at Example III. The above discussion accompanied by Section III would enable those skilled in the art to identify and isolate those plants that express HSP22 in heat stress conditions so that plants can be selected that better tolerate heat stress due to the chaperone characteristics of HSP22.

The antibodies and fragments thereof are useful for diagnostic assays to detect amounts of HSP22 present in whole leaf samples. A person skilled in the art will readily recognize that combinations can be put together that would allow an individual to test a particular plant's ability to tolerate heat stress. These combinations include an aliquot of an antibody or fragment thereof that specifically binds to a portion of HSP22. The combination further comprises an immunologic detection reagent such that identification of HSP22 levels can be determined. Additionally, nucleic acid probes could be utilized to determine levels of HSP22 mRNA and one skilled in the art will readily recognize that combinations can be formed to utilize nucleic acid probes for testing heat stress resistance.

PURIFICATION AND ANALYSIS OF MITOCHONDRIAL HSP22 FROM MAIZE

Figure 15:
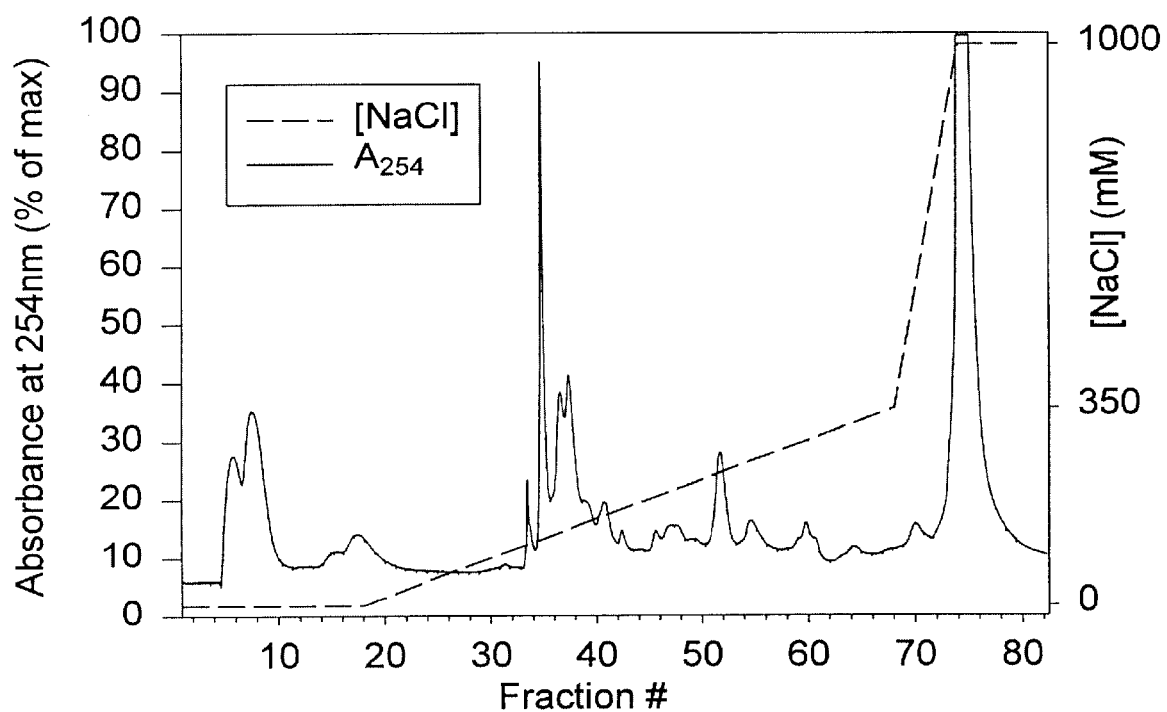
FIGS. 15A–15C, FIG. 15A illustrates the UW trace and the salt gradient from the elution profile from membrane fractions isolated from heat-shocked mitochondria containing HSP22 protein applied to a Pharmacia FPLC Mono-Q anion exchange column and eluted with a linear NaCl gradient from 0 to 350 nm.

Purification of HSP22 was done using anion exchange chromatography. The upper panel of FIG. 15 depicts the UV trace and the salt gradient from the elution profile of HSP22. SDS-PAGE gels of the HSP22 containing fractions collected were either stained with Coomassie blue, as seen in the middle panel of FIG. 15, or transferred to nitrocellulose and probed with affinity purified HSP22 polyclonal antibody, as seen in the lower panel of FIG. 15. The elution profile appears to vary occasionally, resulting in the presence of other proteins in the HSP22 peak fractions. Cpn60 is one of the proteins that occasionally appears in these fractions. Subsequent chromatography of the pooled HSP22 peak on a hydrophobic interaction column (Phenyl Superose) removes nearly all other proteins except cpn60. The anion exchange methods are disclosed in Example V.

Figure 16:
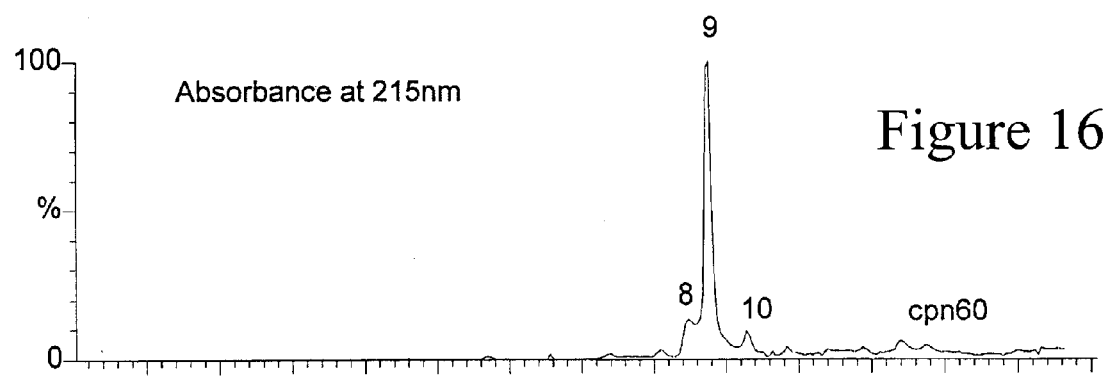
FIGS. 16A–16C, FIG. 16A depicts the pooled HSP22 peak recovered by Mono-Q followed by Phenyl Superose chromatography which was concentrated and applied to a C8 microbore reverse-phase HPLC column, the column was eluted with a 2% to 60% (v/v) acetonitrile/$H_2O$ gradient containing 0.1% (v/v) TFA. The eluate was directed through a 1:10 splitter with 90% of the elute passing through a UV flow cell and collected.
Figure 16:
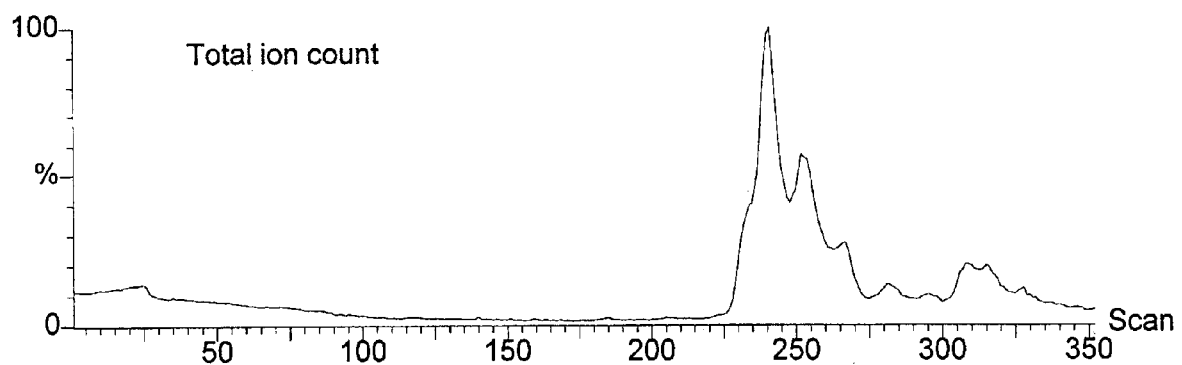
Figure 16:
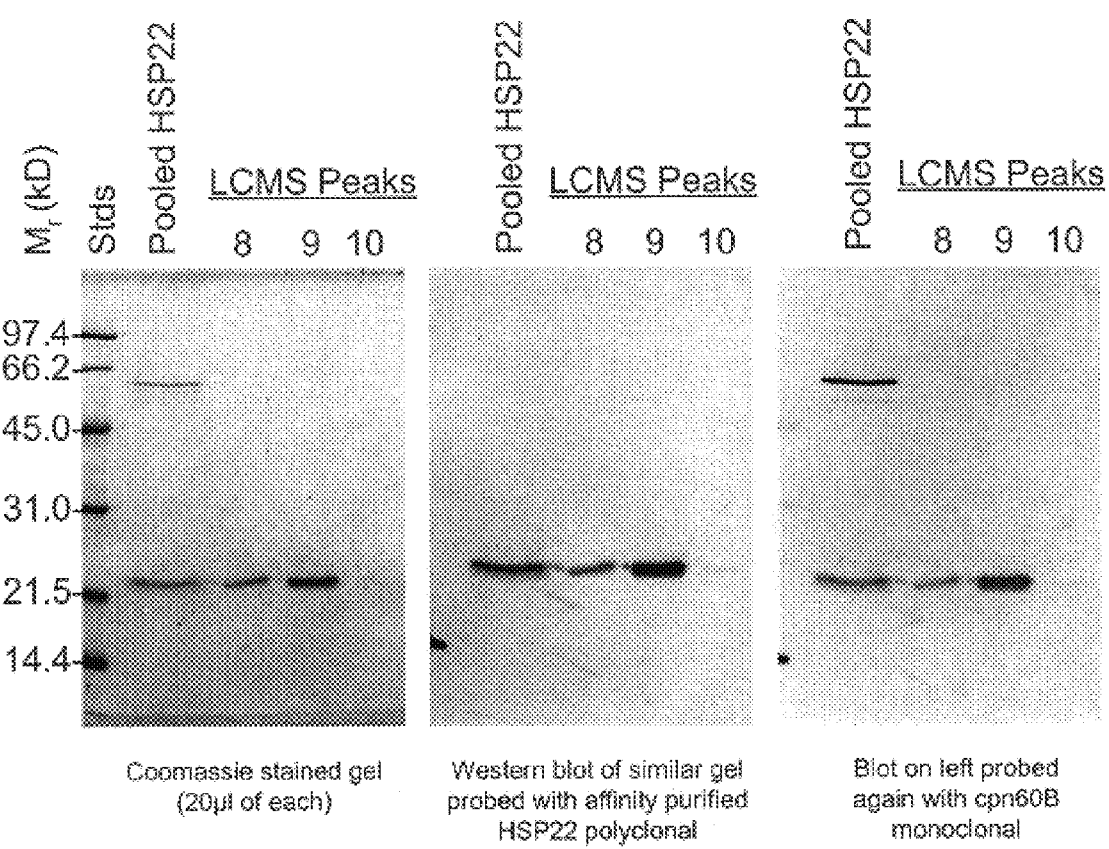

An analysis was then done on the purified HSP22 by reverse phase liquid chromatography and electrospray ionization mass spectroscopy. FIG. 16A depicts the elution profile measured at 215 nm. The most prevalent peaks were collected and labeled as 8, 9, and 10. The remaining sample was subjected to real-time analysis on a VG Platform mass spectrometer utilizing an electrospray ionization source and a quadrapole analyzer with an 8-second scan time from 700–1800 m/z. FIG. 16B represents the total ion count that was detected by the instrument. The observed downshift of peaks and band broadening were due to the eluates travel time to the detector. FIG. 16C illustrates a Coomassie-stained SDS-PAGE gel of 20 µl aliquot from the sample applied to the column and the three fractions (8, 9, and 10) that were recovered. To ensure that these proteins were HSP22, a similar gel was immunoblotted with the affinity purified HSP22 polyclonal at FIG. 16C middle panel. This blot demonstrates that both peak 8 and peak 9 contain HSP22. After recording the blot, the same gel was reprobed with the cpn60B monoclonal antibody. This is shown in FIG. 16C in the lower right panel which reveals that cpn60 was present in the sample prior to chromatography and that it was not present in peaks 8, 9, and 10. Analysis of the mass spectrum data showed that scans 303–321 contained proteins with masses of 57,650 and 57,870 and are likely to be the cpn60 component.

Figure 18:
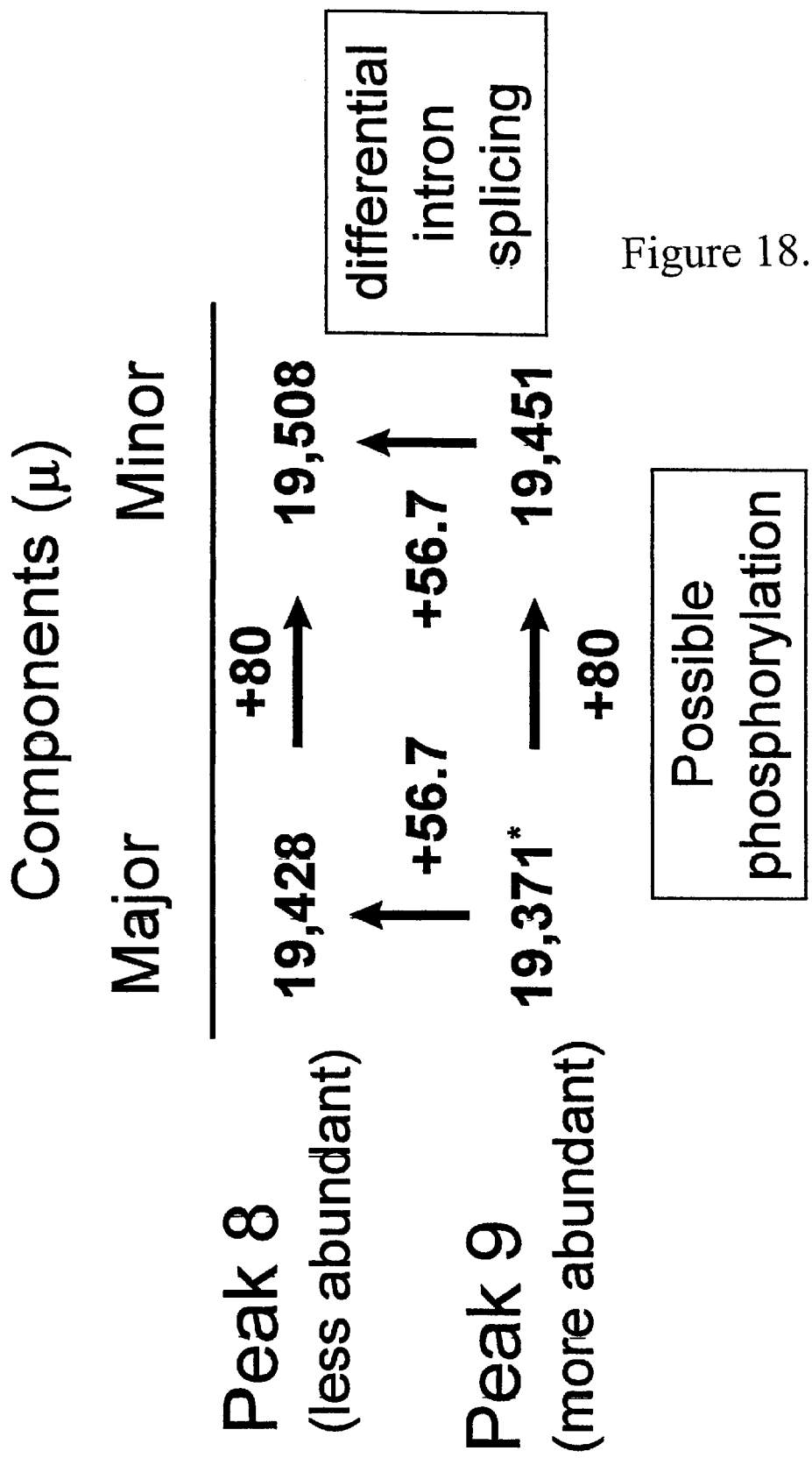
FIG. 18 is a schematic representation of the four potential forms of HSP22 revealed in the mass spectral data gathered from peaks 8 and 9. The 80 Da difference in the two components of both peaks 8 and 9 indicates a phosphorylation. Comparison of the two primary components of peaks 8 and 9 reveals a mass difference of 56 Da, which is most likely due to alternative intron splicing of the cDNA.

The mass spectral data from peaks 8 and 9 were analyzed using the MassLynx software package. Scans 228–233, representing analysis of the peak 8 protein, were combined and this mass spectrum is illustrated in FIG. 17A. The raw spectrum was transformed to reveal the masses of the proteins in peak 8, as shown in FIG. 17B. Peak 8 was found to be primarily composed of a protein with mass 19,428 Da and less abundant components with masses of 19,370 and 19,508 Da. The raw data for peak 9 is shown in FIG. 17C and is the combined scans 236–242. The transformed data shown in FIG. 17D reveals that there are two major components present, with the major being at 19,371 and the minor at 19,451 Da. The 19,370 Da component of peak 8 appears to be the major component in peak 9 and is probably due to incomplete separation of the two peaks. The difference between the remaining two components in both peak 8 and peak 9 is 80 Da, which may indicate a phosphorylation. Comparison of the two primary components of peak 8 and peak 9 reveals a mass difference of 56.7 Da. This mass difference is most likely due to differential intron splicing of the cDNA. A schematic of the four potential forms of HSP22 is shown at FIG. 18. Methods for the online reverse phase HPLC-MS are disclosed at Example VI.

PEPTIDE SEQUENCING OF PURIFIED HSP22

The relevant peaks from the C8 microbore reverse-phase HPLC column were sequenced using trypsin. The tryptic digestions of the peaks were found to have several peptide fragments of common mass and are thus believed to be very similar. Tryptic peptides that were the same between the peaks were subjected to FAB-MS/MS sequencing. To date, four tryptic peptides with masses of 727.4, 815.4, 1088.5, and 1285.7 have been sequenced. Previously, N-terminal amino acid was sequenced from the HSP22 spots by Edman degradation off of protein blots. BioLynx software was used to obtain the molecular mass of tryptic peptides present in the N-terminal amino acid sequence. Only one tryptic fragment was present and it was the N-terminus with a mass of 727.4. One reason why the tryptic peptide of mass 727.4 was sequenced by FAB-MS/MS was to confirm the N-terminal sequence and to link the two experiments. Methods for peptide sequencing are disclosed at Example VII.

ISOLATION AND CHARACTERIZATION OF HSP22 CDNA

A cDNA expression library was prepared from heat-shocked etiolated maize seedlings using the UniZAP XR phage lamda expression vector kit from Stratagene. The library was constructed using mRNA from heat-stressed etiolated maize seedlings. This expression library was initially screened with the HSP22 monoclonal antibody and one positive (P8) was obtained. After in vitro excision of the selected phage, the plasmid (ZmHSP22P8) was sequenced from both directions. Cloning and sequencing methods are disclosed at Example VIII.

As seen in FIG. 19, the sequence for the ZmHSP22P8 clone was found to contain the entire mature HSP22 protein coding sequence, bases 214–735, and the 3' untranslated region, bases 736–1028, and a 15 bp polyadenylated tail, which is not shown. The N-terminal sequence identified for spots HSP22A and B matched this sequence exactly and identified HSP22 spot B residue 18 as Ser. Six more clones have now been sequenced and have a sequence similar to the P8. One of these clones had an additional 15 amino acids of transit peptide and these have been added to the P8 sequence. In an effort to obtain the full sequence for the transit peptide, the P8 clone was used as a probe to screen the library again. Twenty-four additional clones of various lengths were obtained after screening $3.2 \times 10^5$ plaques. All clones were sequenced and all but one contained sequence identical to the P8 clone, but none contained the full transit peptide. The one odd clone showed signs of differential intron splicing resulting in the +56.7 D shift in molecular weight as observed by mass spectrometry. Comparison of the incomplete HSP22 cDNA molecule to the Maize Expressed Sequence Tag Database developed by Pioneer Hi-Bred International allowed identification of three clones that contained identical sequence to the N-terminal region of the mature HSP22 protein. Two of these clones extended the molecule to include a putative N-terminal transit peptide and 78 nt of the 5' untranslated region, which is shown by the underlined nucleotides in FIG. 19. The predicted protein molecule for the entire coding portion of the putative HSP22 precursor cDNA and the cDNA nucleotide molecule are also shown in FIG. 19. The predicted mass of the entire 218 amino acid molecule is 23,816 D.

Figure 20:
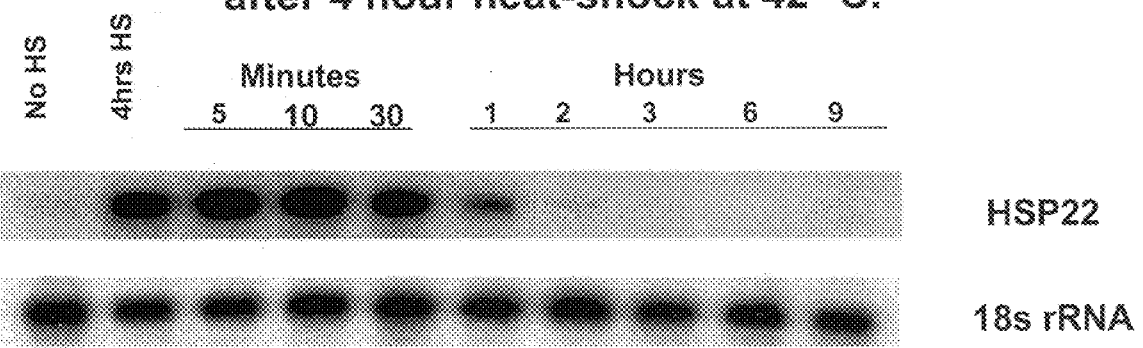
FIG. 20 depicts HSP22 northern blot analysis of results from experiments where the P8 cDNA clone was used as a probe to investigate levels of HSP22 mRNA. Seedlings were subjected to heat stress at 42° C. for four hours and then returned to normal growth temperature for recovery. mRNA was isolated at 5, 10, and 30 minutes after the start of the recovery period, and then at 1, 2, 3, 6, and 9 hours of recovery. HSP22 mRNA levels remained high for 5-, 10- and 30-minute time points, but had dropped significantly after one hour of recovery. The bottom panel depicts the 18s rRNA control for loading which demonstrates that the 18s rRNA levels were similar in all of the lanes.
Figure 23:
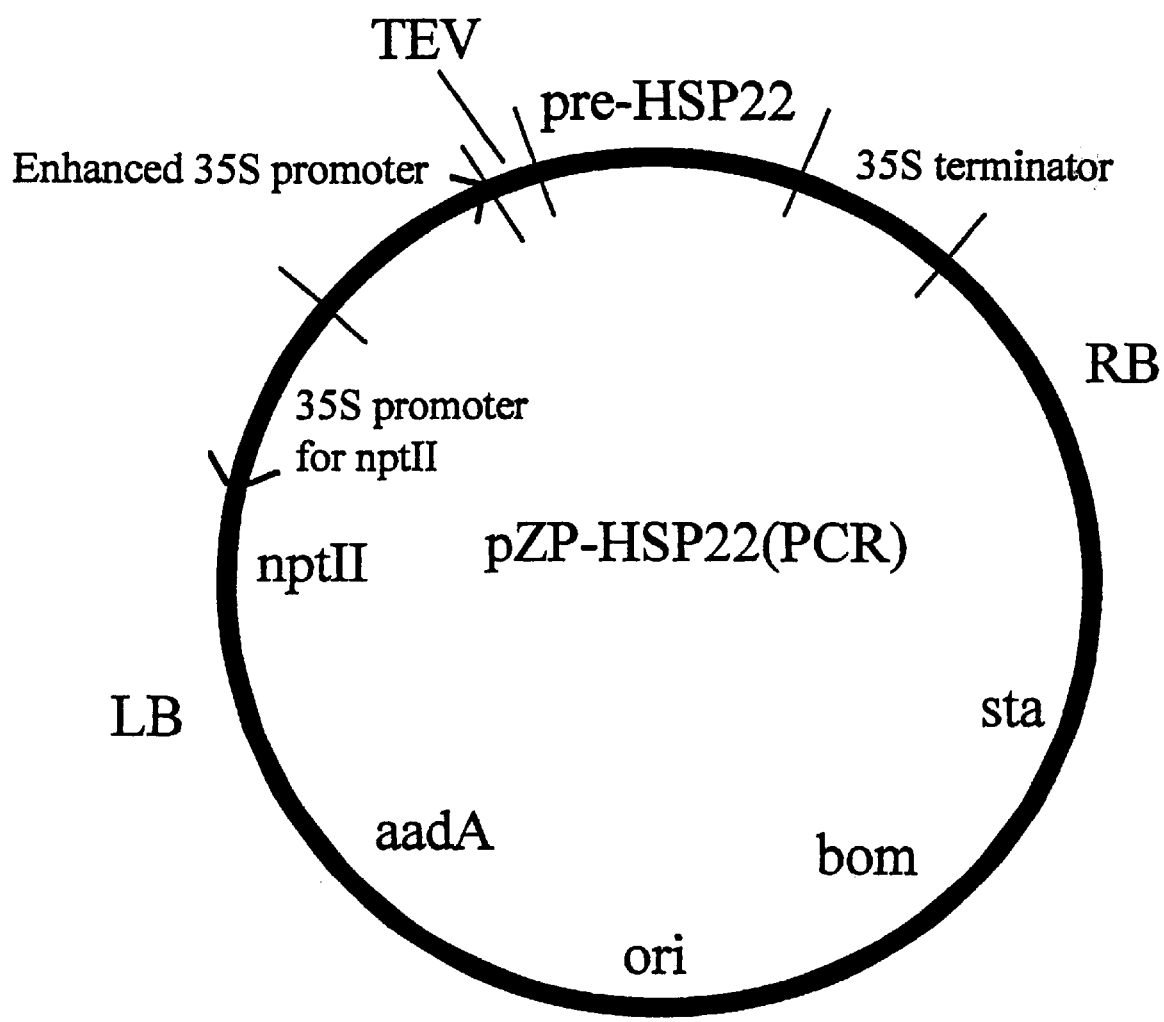
FIG. 23 illustrates the vector containing the partial genomic nucleic acid molecule illustrated in SEQ. ID. NO. 4.

In addition to utilizing the monoclonal antibody, the P8 cDNA clone was utilized as a probe to investigate levels of HSP22 mRNA in experiments similar to those described earlier where HSP22 protein levels were evaluated with immunoblots. Example IX discloses the method for using probes to determine HSP22 expression levels. Etiolated seedlings were subjected to heat stress at 42° C. for four hours and then returned to the normal growth temperature for recovery. mRNA was isolated at 5, 10, and 30 minutes after the start of the recovery period and then at 1, 2, 3, 6, and 9 hours of recovery. FIG. 20 illustrates the northern blot analyses of these experiments. HSP22 mRNA levels remained high for 5-, 10-, and 30-minute time points, but had dropped significantly after one hour of recovery. A probe was used against the 18s rRNA as a control for RNA loading. The lower panel of FIG. 23 demonstrates that levels of 18s rRNA were similar in all of the lanes. These experiments demonstrate that, during the relief of stress, the half life of HSP22 mRNA is less than one hour. Those of ordinary skill in the art would know that any nucleic acid molecule that hybridizes to HSP22 mRNA will allow similar results.

Figure 21:
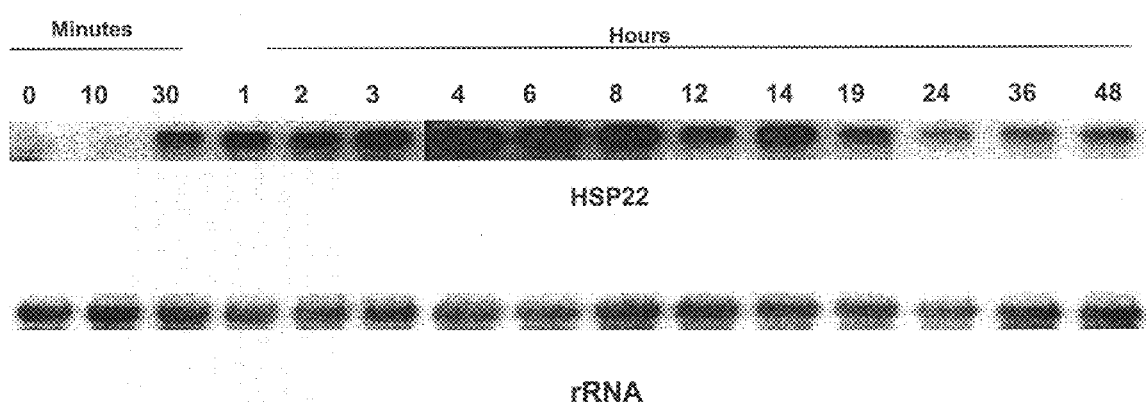
FIG. 21 depicts HSP22 northern blot analysis from experiments where the P8 cDNA clone was used as a probe to investigate levels of HSP22 following continuous heat shock treatment at 42° C. mRNA was isolated at 0, 10, and 30 minutes, and then at 1, 2, 3, 4, 6, 8, 12, 14, 19, 24, 36 and 48 hours after the onset of heat stress. HSP22 mRNA was first observed after 30 minutes, and the levels peaked at four to six hours of heat stress.

Northern blots were prepared from an experiment following a continuous heat shock treatment at 42° C. Etiolated seedlings were exposed to 42° C. and mRNA extracted at 0, 5, 10, and 30 minutes and 1, 2, 3, 4, 6, 8, 12, 19, 24, 36, and 48 hours after the onset of heat stress. The results of this experiment are given in FIG. 21. Significant levels of HSP22 mRNA were observed after 30 minutes and levels peaked at four to six hours of stress. Thereafter, the levels of HSP22 mRNA decreased becoming low at 19 to 24 hours after the imposition of stress.

Those skilled in the art would appreciate that this probe, along with the methods in example X, can be utilized in experiments designed to identify and isolate particular plants that express HSP22 in heat stress conditions so that plants can be identified that are more heat tolerant due to the chaperone characteristics of HSP22. Additionally, those skilled in the art will readily recognize that combinations can be put together that would allow an individual to test a particular plant's ability to tolerate heat stress. These combinations would include an aliquot of a nucleic acid molecule that hybridizes to a portion of HSP22 mRNA. The combination would further comprise a detection method used to identify the bound nucleic acid. Those skilled in the art will recognize that there are many different detection methods that may be utilized such as the one illustrated in example IX. Additionally, one skilled in the art would be able to make nucleic acid probes from the disclosed sequence that would work as well as the preferred embodiment disclosed above.

Figure 22:
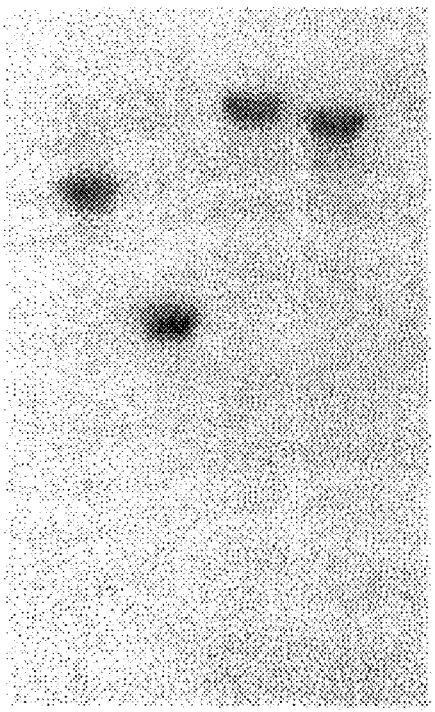
FIG. 22 depicts experiments where the P8 probe was used on southern blots to evaluate the copy number of the genomic copy of the gene. The genomic DNA was probed with mature HSP22 protein cDNA. The procedure utilized seven different restriction enzymes. Because only one band was observed with each restriction enzyme on the southern, the probe most likely recognized only one gene.

Evaluation of the copy number for mitochondrial HSP22 was conducted with southern blots. The P8 probe was used on the southern blots to evaluate the copy number of the genomic copy of the gene. Seven different restriction enzymes were used and only one band was observed on the southern blot, indicating that the probe most likely recognizes only one gene, as seen in FIG. 22.

ISOLATION OF HSP22 PARTIAL GENOMIC

A partial genomic for HSP22 was isolated utilizing a 3' and a 5' primer designed with information from SEQ. ID. NO.: 1. The primers were utilized in a PCR amplification with purified heat stressed etiolated maize seedling genomic DNA. The partial genomic comprises SEQ. ID. NO. 4. The methods for the production of the partial genomic are described at Example X.

SEQ. ID. NO. 4 was cloned into an expression vector and used to transform *E. coli* cells. One of ordinary skill in the art knows that there are many vectors and host cells that could be utilized.

Additionally, SEQ. ID. NO.: 4 was cloned into a vector designed for transforming plants such as tobacco and Arabidipsis. Methods for both the vector and transformations are described in Example XI.

EXAMPLE I

Isolation of Mitochondria, Cytoplasmic Proteins, and Chloroplasts

Maize (*Zea mays* L. inbred B73) seeds were imbibed for three days, planted 1 cm deep on a 3 cm bed of coarse vermiculite in 25×40×15 cm trays, covered with a well-ventilated lid, and grown at 29° C. for three days in the dark. For heat-shock experiments, entire trays were placed in a high temperature incubator for the desired duration. Mitochondria were isolated from etiolated shoots of maize as previously described (Hayes et al., Plant Physiology 97:1381–1387, 1991; Luethy et al., Plant Physiology 97:1317–1322, 1991). The protein content of various fractions was measured using the Lowry procedure as modified by Larson et al., Analytical Biochemistry 155:243–248, 1986. Isolated mitochondria were suspended in a medium consisting of 250 mM sucrose and 30 mM Mops (pH 7.2). Mitochondria were sub-fractionated into membranes, soluble proteins, and soluble proteins that are part of large complexes as described by Hayes et al., Plant Physiology, 1991, 97:1381–1387. The cytoplasmic fraction of etiolated maize shoots was obtained during isolation of mitochondria as the supernatant from the second centrifugation step (20,000×g for 5 min) that initially pellets the mitochondria. This supernatant was concentrated two-fold above a Centricon-10 membrane (Amicon) before use.

Maize chloroplasts were isolated using a combination of procedures from Leegood and Walker, Plant Physiology 63:1212–1214, 1979 and Mourioux and Douce, Plant Physiology 67:470–473, 1981. Maize seeds were imbibed, planted in vermiculite and watered as needed for two weeks in a growth room with a 12 h photoperiod under fluorescent lighting (PPFD=130–160 $\mu$mol m$^{-2}$ s$^{-1}$). The ambient temperature was 21° C./13° C. (light/dark). Fifty grams of leaves were cut transversely with a razor blade into 1 cm segments and placed into 150 $\mu$l of semi-frozen grinding medium (330 mM mannitol, 10 mM EDTA, 5 mM MgCl$_2$, 0.2% (w/v) sodium D-isoascorbate, and 30 mM Mops pH 7.6) and homogenized with three two-s bursts at full speed in a Waring blender. The brei was squeezed through two layers of cheesecloth and allowed to drip through eight layers of muslin wetted with grinding medium. The homogenate was centrifuged in a SS-34 rotor at 6,000×g for 90 s. Crude chloroplast pellets were re-suspended in 5 $\mu$l of 1× Percoll gradient buffer (330 mM mannitol, 2 mM EDTA, and 50 mM Mops pH 7.8) and layered on top of two 25 $\mu$l 50% Percoll (12.5 $\mu$l 2× Percoll gradient buffer and 12.5 $\mu$l Percoll each) gradients that had been pre-centrifuged for 2 h at 10,000×g in an SS-34 rotor. The crude chloroplasts were then centrifuged on the gradients for 10 min at 5,000×g and the intact chloroplasts were collected from the rapidly sedimenting diffuse green band. The purified chloroplasts were diluted by adding 2 volumes of 1× Percoll gradient buffer and pelleted in a microfuge at 3,500×g for 90 s. The supernatant was aspirated and the chloroplasts re-suspended in a minimal volume of 30 mM Mops pH 8.0 and stored at −80° C. for subsequent gel analysis.

One- and Two-Dimensional Gel Electrophoresis

One dimensional SDS-PAGE was performed with a Bio-Rad Mini-Protean II apparatus using a 14% (w/v) resolving gel and a 5% (w/v) stacking gel. Other conditions are as described by Elthon and McIntosh, Plant Physiology 82:1–6, 1986. Molecular mass markers used were Bio-Rad Low Molecular Weight Standards. Two-dimensional IEF/SDS-PAGE was performed as described by Barent and Elthon, Plant MolecularBiology Reporter 10:338–344, 1992. Pharmalyte 3–10 ampholytes (Pharmacia) were used in the first dimension.

EXAMPLE II

Polyclonal Antibodies, Monoclonal Antibodies, and Immunoblotting

Polyclonal antiserum was raised in mice against purified E. coli DnaK protein as described by Krska et al., Journal of Bacteriology 175:6433–6440, 1993. Rabbit polyclonal sera produced against maize mitochondria cpn60 was a gift from Dr. T. Prasad, Iowa State University, Ames, Iowa, USA. Polyclonal sera raised to an over-expressed fusion protein of maize enolase was a gift from Dr. D. T. Dennis, Queens University, Ontario, Canada. Antibodies raised to NADP-malate dehydrogenase were a gift from Dr. R. Chollet, Univ. of Nebraska, Lincoln, Nebr., USA. Polyclonal antisera for the mitochondrial HSP22 proteins were produced by injecting proteins electro-eluted from the separate HSP22A and HSP22B protein spots cut out after Coomassie blue visualization of 2D SDS-PAGE gels. For each mouse injected, protein spots from eight gels were electro-eluted using the Bio-Rad 422 Electro-Eluter fitted with 12.5 kD cut-off membrane caps at 10 mA per sample for 3 h.

For the production of the HSP70, cpn60 and $\beta$-ATPase subunit MAbs, female BALB/C mice were immunized with whole maize mitochondrial proteins. Mice producing HSP22 polyclonal antisera were used for the HSP22 monoclonal line development. Hybridomas were produced according to Elthon et al., Plant Physiology 89:1311–1317, 1989 except that growth media contained 20% (v/v) fetal calf serum, 2 mM L-glutamine, 25 $\mu$g/l ampicillin, 100 $\mu$g/l streptomycin sulfate, and 0.1% (w/v) amphotericin B in a base culture medium of 1× Dulbecco's Modified Eagle's Medium (Sigma). Hybridomas secreting useful antibodies were selected using immunoblots of mitochondrial proteins. Culture supernatant containing the MAbs was stored at −80° C. and used at a 1:10 dilution. For immunoblots, protein gels were transferred to nitrocellulose and probed with antibodies according to Hayes et al., Plant Physiology 97:1381–1387, 1991. Goat anti-mouse IgG and anti-rabbit IgG antibodies conjugated with alkaline phosphatase were purchased from Sigma. Proteins transferred to nitrocellulose were reversibly visualized by staining with 0.2% (w/v) Ponceau S in 3% (w/v) TCA for 2 minutes followed by rinsing with distilled H$_2$O. Blots were fully destained prior to antibody probing by washing with PBS containing 0.3% (v/v) TWEEN-20.

Methods for producing fab or f(ab')$_2$ fragments are well-known in the art. The methods used for this work are described by Pierce Chemical Company, Rockford, Ill., which is hereby incorporated by reference.

EXAMPLE III

Detection of HSP22 in Whole Leaf Samples

Leaf samples were frozen in dry ice as collected and stored at −80° C. until used. One gram of plant tissue was ground in liquid nitrogen in a mortar and pestle until a fine powder was achieved. For standard immunoblot assays, the powders were extracted with 1× SDS-PAGE sample buffer and centrifuged in a microfuge at maximum speed for 5 min. The supernatants were used to run standard SDS-PAGE gels for immunoblot analysis. For ELISAs, the fine powder was extracted with 30 mM MOPS (pH 8.0). In some instances, the fine leaf powders were resuspended in the normal grinding medium and subjected to the first two centrifugation steps of mitochondrial isolation. The crude mitochondrial pellets were resuspended in ddH$_2$O and subjected to standard SDS-PAGE and immunoblot analysis.

For detection of mitochondrial HSP22 using an ELISA, 20 $\mu$l of extracted samples were placed in separate wells of 96 well ELISA plates. The solutions PBS, PBS-Tween, and pH 9.5 buffer are as described by Elthon and McIntosh, PNAS 84:8399–8403, 1987. PBS (200 $\mu$l was added to each well and the plate incubated overnight at 4° C. The solution was then shaken out of the plate and the plate rinsed with PBS-Tween twice. The HSP22 monoclonal antibody or antibody fragments were added to each well as a 1/10 dilution in PBS-Tween (200 $\mu$l per well). The plate was incubated for 4 hours at 4° C. The solution was then shaken out of the plate and the plate rinsed with PBS-Tween twice. Secondary antibody (anti-mouse alkaline phosphatase) was added to each well at a 1/1000 dilution in PBS-Tween (200 $\mu$l per well). The plate was incubated at 4° C. for 2 hours. The plate was shaken out and rinsed three times with PBS-Tween. The plate was then rinsed with pH 9.5 buffer. pNPP (para-nitrophenyl phosphate) substrate was prepared as a 0.8 $\mu$g/$\mu$l solution in pH 9.5 buffer and 200 $\mu$l added to each well and color developed before reading at 405 nm.

EXAMPLE IV
Purification of Mitochondrial HSP22 Using Monoclonal Antibody Affinity Chromatography HSP22 monoclonal antibody was purified using a FPLC protein G Superose column. The column was equilibrated with 20 mM phosphate buffer at pH 7.0 and the antibody solution applied. The column was washed with phosphate buffer until all unbound proteins were eluted. The monoclonal antibodies were then eluted with 100 mM glycine at pH 2.7. The eluted monoclonal antibodies were collected and neutralized to pH 7.0.

An antibody affinity column was prepared using 4 mg of protein G Superose-purified HSP22 monoclonal antibody in a minimal volume of PBS. The antibody was bound to 1 $\mu$l of protein A Sepharose 4B beads and crosslinked for 1 hr using 20 mM diethylpimelimidate in 200 mM triethanolamine, pH 8.2. The anti-HSP22 beads were washed with PBS and pre-eluted with 50 mM CAPS buffer, pH 11.5, prior to addition of sample. Mitochondria (HS mito) from 4 hr heat-stressed seedlings were isolated, sonicated in 2 $\mu$l PBS, and centrifuged to remove the membrane (HS membrane) fraction (Hayes et al., Plant Physiology 97:1381–1387, 1991. The cytoplasmic fraction (HS cytoplasm) was isolated according to Lund et al., Plant Physiology 116:1097–1110, 1997. Approximately 5 mg of mitochondrial matrix proteins (HS matrix) was applied to the anti-HSP22 column and the proteins which did not bind were collected (HS matrix flow thru). The anti-HSP22 column was washed with 50 mM CAPS buffer pH 11.5 to elute essentially pure HSP22.

EXAMPLE V
Chromatographic Purification of HSP22

Isolated mitochondria were suspended in a medium consisting of 250 mM sucrose and 30 mM Mops (pH 7.2). Mitochondrial membranes were removed by sonication of 6 $\mu$g of washed mitochondria in 1 $\mu$l of 30 mM Mops pH 8.0 followed by ultracentrifugation in a TLA-100.2 rotor (Beckman) for 30 min at 100,000×g. The supernatant contained the soluble mitochondrial proteins and the large protein complexes as described by Hayes et al., Plant Physiology 97:1381–1387, 1991. Approximately 5 $\mu$g of mitochondrial proteins (afterremoval of the membrane fraction) from heat stressed maize seedlings was applied to a Pharmacia FPLC HR5/5 Mono-Q anion exchange column. The column was washed at a flow rate of 0.5 $\mu$l min$^{-1}$ with 10 $\mu$l of 30 mM Mops pH 8.0 and then developed with a 25 $\mu$l linear gradient to 35% (v/v) 1 M NaCl, 30 mM Mops pH 8.0. The gradient was increased to 100% (v/v) 1 M NaCl, 30 mM Mops pH 8.0 during the following 3 $\mu$l and then maintained at 100% (v/v) 1 M NaCl, 30 mM Mops pH 8.0 for 5 $\mu$l. The eluate was analyzed using a UV flow cell with a 1 cm path-length and an illuminated volume of 8.7 $\mu$l and collected in 0.5 $\mu$l fractions. The samples were analyzed for the presence of HSP22 using SDS-PAGE immunoblots. The HSP22 containing fractions were pooled and concentrated using an Amicon device with a 10 kD cut-off membrane (YM-10 Diaflo Ultrafilter, Amicon, Beverly, Mass., USA.). Solid NaCl was added to the pooled fraction to a concentration of 4M and the sample applied to a hydrophobic interaction column (Pharmacia HR5/5 Phenyl Superose) equilibrated with 4M NaCl, 30 mM Mops pH 8.0. Nearly pure HSP22 was collected from the column eluate prior to application of a decreasing salt gradient. The HSP22 containing fractions were again pooled and concentrated using the same Amicon device.

EXAMPLE VI
Online Reverse Phase HPLC-MS (High Pressure Liquid Chromatography—Mass Spectrometry) Analysis of Purified HSP22

The pooled and concentrated HSP22 peak recovered from Phenyl Superose chromatography was applied to a Gilson HPLC (Gilson Inc. Middleton, Wis., USA) fitted with a C8 microbore (1.0×50.0 mm Zorbax C8 300 Å) reverse-phase HPLC column and the column developed at 50 $\mu$l min$^{-1}$ over 40 min with a 2–60% (v/v) acetonitrile/ddH$_2$O gradient containing 0.1% (v/v) trifluoroacetic acid. Through the use of a splitting tee, 90% (v/v) of the eluate was directed through a UV flow cell (0.5 $\mu$l illuminated volume) with the detector response set to 0.02 AU full scale. The other 10% (v/v) of the sample was analyzed on a Micromass Platform II mass spectrometer (Micromass, Manchester, UK) utilizing an electrospray ionization (ESI) source and a quadrapole analyzer with an 8 second scan time from 700–1800 m/z. The detector was calibrated using horse heart myoglobin (MW 16,951.4±0.5 D) and was found to be accurate to ±0.01%. Mass spectra were analyzed using the MassLynx software (Micromass, Manchester, UK).

EXAMPLE VII
Sequencing of HSP22 Tryptic Peptides Using CID MS/MS

HSP22 Peak I and Peak II samples from HPLC were lyophilized and each digested with freshly prepared trypsin (treated with n-tosyl-L-phenylalanine chloromethyl ketone) (T-8642 Sigma) at 25:1 HSP22/trypsin molar ratio in 0.1 M Tris pH 7.8 for 4 hr at 37° C. N-tosyl-L-phenylalanine chloromethyl ketone inhibits the chymotryptic activity (non-specific cleavage at aromatic amino acids) of trypsin, therefore trypsin cleaves the protein only at the C-terminal side of Arg and Lys residues. The tryptic peptides were separated and analyzed using the online HPLC-MS system described above but using a microbore C18 reverse phase column and developed with a gradient of 2–40% (v/v) acetonitrile/ddH$_2$O containing 0.1% (v/v) TFA over 40 min at a flow rate of 50 $\mu$l min$^{-1}$. The Platform II mass spectrometer was calibrated with NaI using an 8 second scan time from 400–2000 m/z. Peptide mass determinations are accurate to ±0.3 D. Tryptic peptides were sequenced using CID MS/MS on a Micromass AutoSpec (Micromass, Manchester, UK) fitted with an orthogonal acceleration time of flight analyzer (oaTOF) using FAB as the source of ionization. A 2 $\mu$l aliquot of the fraction containing the tryptic peptide of interest was mixed with a small amount of 1:1 (v:v) glycerol/thioglycerol and placed on the FAB probe and desorbed using a 25 keV cesium ion beam. The monoisotopic (M+H)$^+$ ions of the peptides of interest were selected by the first MS, the double focusing magnetic sector instrument, and then guided into the collision cell where the ions are collisionally activated by interactions with xenon. The masses of the resulting fragments were determined by the second mass spectrometer, the oaTOF analyzer. Masses of fragment ions were used to determine peptide amino acid composition and sequence. This technique for sequence determination is described in depth by Papayannopoulos, Mass Spectrometry Reviews, 14:49–73, 1995. Because this technique relies solely on the masses of the amino acids, their side chains, and fragmentation products, the isomeric amino acids Leu and Ile cannot be readily distinguished.

Mitochondrial HSP22 Protein N-Terminal Sequencing

Washed mitochondria from heat stressed etiolated seedlings were separated on 2D gels (300 $\mu$g per gel) and transferred to PVDF membranes as described by Dunbar et al., Plant Molecular Biology Reporter 15:46–61, 1997. The total protein profile was visualized by amido black staining and the spots corresponding to HSP22A and HSP22B were cut out and sequenced by Edman degradation according to Dunbar et al., Plant Molecular Biology Reporter 15:46–61, 1997.

Protein and Nucleotide Sequence Analysis and Comparison

All sequence analysis and comparison was performed with the Wisconsin Package Version 9.0, Genetics Computer Group (GCG), Madison, Wis., USA. Protein molecular mass predictions were performed using the BioLynx software package (Micromass, Manchester, UK).

EXAMPLE VIII

Cloning and Sequencing of HSP22 cDNA

Total RNA was isolated from etiolated maize mesocotyls using TRIzol reagent (Life Technologies, Grand Island, N.Y., USA) as described by the manufacturer's published protocol for use with whole tissues. The total RNA extracts were applied to Oligotex poly dT beads (Qiagen Inc., Chatsworth, Calif., USA) and the mRNAs were purified as described in the manufacturer's protocol. A cDNA expression library was created using the ZAP-cDNA Gigapack Gold Cloning kit (Stratagene, La Jolla, Calif., USA) with mRNAs isolated from 3-day-old etiolated maize (inbred B73) mesocotyls that were grown at 29° C. and heat shocked at 42° C. for 2 hours. The library was screened using the monoclonal antibody for HSP22 using the picoBlue immunoscreening protocol (Stratagene, La Jolla, Calif., USA). DNA sequencing was done using Thermo Sequenase and cycle sequencing using infrared dye-labeled dATP according to the protocol of the manufacturer, which is Amersham Corporation (2636 S. Clearbrook Drive, Arlington Heights, Ill., 60005). The sequence was analyzed using a model 4000(L) sequencing apparatus, which was run according to the protocols of the manufacturer, which is LI-COR (4421 Superior Street, Lincoln, Nebr. 68504).

EXAMPLE IX

Northern and Southern Blot Hybridization

The HSP22 probe was produced by digesting the HSP22 clone N27 (which contains only the C-terminal 10 residues of HSP22 and the entire 3' UTR) with EcoRI and DraI to release a 319 nt fragment. The fragment was separated from the vector sequence using Geneclean (Biol101, Vista, Calif.) and was labeled with $^{32}$P using the random primer extension method, Prime-It II (Stratagene, La Jolla, Calif., USA), and used as a HSP22 specific probe. The rRNA probe was produced in a similar fashion using a 1.25 kb fragment of the *Saurumatum guttatum* (Schott) 26S rRNA gene. All northern blot procedures were performed essentially according to Selden, In Ausubel et al., eds., Current Protocols in Molecular Biology, Wiley, 4.9.1–4.9.5, 1987. Following the heat stress treatment, seedling mesocotyl regions were excised and immediately frozen in liquid nitrogen and stored at −80° C. until needed. Total cellular RNA was extracted as described above and approximately 8 μg of RNA per lane was separated on 1.2% (w/v) agarose-formaldehyde gels and transferred to Magnagraph nylon membranes (MSI, Westboro, Mass., USA) and fixed by UV cross-linking. Prehybridization was done for at least 2 hours at 42° C. in a solution containing 50% (v/v) formamide, 5× Denhardt solution [100×=2% (w/v) Ficoll 400, 2% (w/v) PVP, 2% (w/v) BSA], 5× SSC [750 mM NaCl, 75 mM Na$_3$ citrate pH 7.0], 1% (w/v) SDS, 2.5% (w/v) dextran sulfate, 50 mM NaH$_2$PO$_4$ buffer, pH 6.8 and 100 μg/μl$^{-1}$ of sheared and denatured salmon sperm DNA. Hybridization was performed in prehybridization solution modified as follows; 1× Denhardt, 5% (w/v) dextran sulfate, 20 mM phosphate buffer, and the radiolabeled probe. The blot was washed at room temperature and then at 68° C. in a solution containing 2× SSPE and 0.5% (w/v) SDS for 15 minutes each. A final wash at 68° C. for 15 minutes in a solution containing 0.2× SSPE and 0.2% (w/v) SDS was followed by autoradiography on X-OMAT AR film using an intensifying screen. Southern blot analysis was formed as described in Sambrook, J., Fritsch, E. F., and Maniatis, T. (1989) In Molecular Cloning: A Laboratory Manual, 2nd Ed., (Cold Spring Harbor, N.Y.: Cold Spring Harbor Laboratory).

EXAMPLE X

Construction of Partial Genomic

Genomic DNA was prepared from heat shocked B73 corn tissue. This was accomplished by utilizing the protocol described in Ausubel, F. M., et. al., (1987), Current Protocols in Molecular Biology, Green Publishing Associates and Wiley-Interscience, New York, pp. 2.3.1–2.3.3, which is hereby incorporated by reference.

The genomic DNA was then utilized as a template in a PCR reaction. The reaction utilized two primers. The 5' primer, designated as HSP-NCO-3F, was a 39 mer comprising SEQ. ID. NO. 2. The 3' primer, designated as HSP-BAM-1R, was a 40 mer comprising SEQ. ID. NO. 3. In the preferred embodiment, the reaction solution was as follows: 20.0 mM Tris-HCl, 50.0 mM KCl, 0.2 mM each of (dATP, dCTP, dGTP, and dTTP), 500 nM SEQ. ID. NO. 2, 500 nM SEQ. ID. NO. 3, 800 ng template DNA, 1.25 units GIBCO/BRL® Taq polymerase, and distilled, deionized water to final volume of 50 μl. The preferred thermocycler conditions were as follows: 1 cycle at 94° C. for 180 seconds, 35 cycles of 94° C. for 45 seconds, then 60° C. for 30 seconds 90 seconds, and 1 cycle at 72° C. for 60 seconds. This reaction produced SEQ. ID. NO. 4, which is a partial genomic nucleic acid molecule for HSP22.

EXAMPLE XI

Vector Construction and Plant Transformation

The partial genomic of SEQ. ID. NO.: 4 was cloned into a pRTL2, which is similar to the pRTL-GUS vector as described in Carrington, J. C. and Freed, D. D., *Journal of Virology*, 64: 1590–1597, 1990, which is hearby incorporated by reference. The only major difference between the pRTL2 vector and the pRTL-GUS vector is the removal of the GUS gene. After SEQ. ID. NO.: 4 has been inserted into pRTL2 a region containing the enhanced 35S promoter, a translation enhancing region from tobacco etch virus (TEV), SEQ. ID. NO.: 4, and the 35S stop region were restriction endonucleased out of the construct with Hind III. The resulting fragment was inserted into the binary vector pZP212. The pZP212 vector is described in Hajdukiewicz et. al., *Plant Molecular Biology* 25: 989–994,1994, which is hereby incorporated by reference. This binary vector construct was introduced into tobacco and Ababidopsis plants utilizing Agrobacterium mediated transfer and leaf disk transformation as described in Horsch, et. al., *Science* 227:1229–1231, 1985, which is hereby incorporated by reference, or vacuum infiltration of intact plants as described in Bechtold et. al., *Acad. Sci.*, Paris, Sci. de la vie/Life Sciences, 316: 1194–1199, 1993, which is hearby incorporated by reference. The Agrobacterium is prepared utilizing the protocol in Ditta, G, et. al., 1980, *Proc. Natl. Acad. Sci.*, USA 77: 7347–7351, which is hearby incorporated by reference.

All references discussed herein are specifically incorporated in their entirety in all respects.

From the foregoing, it will be seen that this invention is one well-adapted to attain all the ends and objects hereinabove set forth together with other advantages which are obvious and which are inherent to the invention. It will be understood that certain features and subcombinations are of utility and may be employed without reference to other features and subcombinations. The above examples discussed the techniques and proceeders used in the current invention are examples, and it is understood that there are many other techniques and proceeders that could be employed that would allow an individual of ordinary skill in the art to perform the claimed invention and that these other techniques and procedures are contemplated by and are within the scope of the claims. Since many possible embodiments may be made of the invention without departing form the scope thereof, it is to be understood that all matter herein set forth, and shown in the drawings are to be interpreted as illustrative and not in a limiting sense.

We claim:

1. A vector comprising a nucleic acid sequence selected from the group consisting of SEQ ID NO: 1, SEQ ID NO: 4, SEQ ID NO: 5 and SEQ ID NO: 7.

2. The vector of claim 1, wherein the vector contains regulatory elements operably linked to the nucleic acid sequence.

3. A plant transformed with the vector of claim 2.

4. The plant of claim 3, wherein the plant is a dicot.

5. The plant of claim 3, wherein the plant is a monocot.

6. The plant of claim 3, wherein the plant is maize.

7. The plant of claim 3 wherein the plant is Arabidopsis.

8. The vector of claim 1 wherein the vector is capable of expressing HSP22.

9. A plant transformed with the vector of claim 1.

10. The transformed plant of claim 9 wherein the transformed plant expresses an amount of HSP22 in excess of that expressed by a nontransformed plant of the same variety under the same conditions.

11. A plant cell transformed with the vector of claim 1.

12. An isolated nucleic acid sequence encoding maize HSP22.

13. An isolated nucleic acid sequence comprising SEQ. ID. NO. 1.

14. An isolated nucleic acid sequence comprising SEQ. ID. NO. 4.

15. An isolated nucleic acid sequence comprising SEQ. ID. NO. 5.

16. An isolated nucleic acid sequence comprising SEQ. ID. NO. 7.

17. An isolated nucleic acid sequence that encodes a protein comprising SEQ. ID. NO. 6.

* * * * *

UNITED STATES PATENT AND TRADEMARK OFFICE
CERTIFICATE OF CORRECTION

PATENT NO. : 6,268,548 B1
DATED : July 31, 2001
INVENTOR(S) : Thomas E. Elthon, Adrian A. Lund, Dinakar Bhattramakki and David Rhoads It is certified that error appears in the above-identified patent and that said Letters Patent is hereby corrected as shown below:

Column 1,
Line 35, delete "20";

Column 5,
Line 64, change "UW" to -- UV --;

Column 17,
Line 46, change "MolecularBiology" to -- Molecular Biology --;

Column 19,
Line 44, change "afterremoval" to -- after removal --;

Column 21,
Line 42, change "Bio1101" to -- Bio 101 --; and

Column 22,
Line 31, change "seconds 90" to -- seconds, then 72° C for 90 --.

Signed and Sealed this

Sixteenth Day of April, 2002

Attest:

JAMES E. ROGAN
Attesting Officer
Director of the United States Patent and Trademark Office

SEQUENCE LISTING

```
<160> NUMBER OF SEQ ID NOS: 7

<210> SEQ ID NO: 1
<211> LENGTH: 1028
<212> TYPE: DNA
<213> ORGANISM: Zea mays
<220> FEATURE:
<221> NAME/KEY: CDS
<222> LOCATION: (79)..(735)
<220> FEATURE:
<221> NAME/KEY: gene
<222> LOCATION: (1)..(1028)
<220> FEATURE:
<221> NAME/KEY: misc_feature
<222> LOCATION: (424)..(693)
<223> OTHER INFORMATION: Heat Shock Domain
<220> FEATURE:
<221> NAME/KEY: exon
<222> LOCATION: (1)..(328)
<220> FEATURE:
<221> NAME/KEY: exon
<222> LOCATION: (329)..(1028)
<220> FEATURE:
<221> NAME/KEY: Poly A_site
<222> LOCATION: (1028)..(1028)
<220> FEATURE:
<221> NAME/KEY: mRNA
<222> LOCATION: (1)..(1028)
<220> FEATURE:
<221> NAME/KEY: source
<222> LOCATION: (1)..(1028)
<223> OTHER INFORMATION: Zea Mays L., Line B73
<220> FEATURE:
<221> NAME/KEY: transit_peptide
<222> LOCATION: (79)..(213)
<220> FEATURE:
<221> NAME/KEY: 3'UTR
<222> LOCATION: (736)..(1028)
<220> FEATURE:
<221> NAME/KEY: 5'UTR
<222> LOCATION: (1)..(78)
<300> PUBLICATION INFORMATION:
<301> AUTHORS: Lund, Adrian A.
       Blum, Paul H.
       Bhattramakki, Dinakar
       Elthon, Thomas E.
<302> TITLE: Heat-Stress Response of Maize Mitochondria
<303> JOURNAL: Plant Physiol.
<304> VOLUME: 116
<306> PAGES: 1097-1110
<307> DATE: 1998-03-00

<400> SEQUENCE: 1
ccacaacagc gaaggagaaa gcagaccaac ctagccaccc agggagaaag aggccaaaag      60
ggaggggaga gtgtcgtc atg gct tcc att gtc gct tcc agg agg gcc gtt     111
                    Met Ala Ser Ile Val Ala Ser Arg Arg Ala Val
                      1               5                  10 cct cta gtt cgc gct ctg gag aag ctc atc gca gcg tcc tcc gct ccc     159
Pro Leu Val Arg Ala Leu Glu Lys Leu Ile Ala Ala Ser Ser Ala Pro
            15                  20                  25 ggg act ggc tcc gcc ctc agg ccg gtg gca gta gcc ggc ggc ctc cgc     207
```

```
                                                        -continued

Gly Thr Gly Ser Ala Leu Arg Pro Val Ala Val Ala Gly Gly Leu Arg
            30                  35                  40 ggc tac aac acc ggc gct ccg ctc cga cgc tac gag ggg gcc gag tcg    255
Gly Tyr Asn Thr Gly Ala Pro Leu Arg Arg Tyr Glu Gly Ala Glu Ser
        45                  50                  55 gaa gac gat agc gtc cgc gag tac gat ggg cgg cac ggc ggc cgg gac    303
Glu Asp Asp Ser Val Arg Glu Tyr Asp Gly Arg His Gly Gly Arg Asp
 60                  65                  70                  75 tac gct gtg ccc agc ctg ttc tca gat att ttc cgt gat ccg ctt agt    351
Tyr Ala Val Pro Ser Leu Phe Ser Asp Ile Phe Arg Asp Pro Leu Ser
                 80                  85                  90 gcg ccg cac agc att ggc cgc ctg ctg aac ctt gtg gac gac ttg gcg    399
Ala Pro His Ser Ile Gly Arg Leu Leu Asn Leu Val Asp Asp Leu Ala
             95                 100                 105 gtg gcg gcg cca ggt cgt gcg gtg cgc cgt ggc tgg aac gcg aag gag    447
Val Ala Ala Pro Gly Arg Ala Val Arg Arg Gly Trp Asn Ala Lys Glu
        110                 115                 120 gac gag gag gcg ctg cac ctg agg gtg gac atg cca ggc ctg ggg aag    495
Asp Glu Glu Ala Leu His Leu Arg Val Asp Met Pro Gly Leu Gly Lys
125                 130                 135 gag cac gtc aag gtg tgg gcg gag cag aac agc ctg gtg atc aag ggc    543
Glu His Val Lys Val Trp Ala Glu Gln Asn Ser Leu Val Ile Lys Gly
140                 145                 150                 155 gag ggc gag aag gag gat agc gag gac gag gcc gcc ccg cct ccg aga    591
Glu Gly Glu Lys Glu Asp Ser Glu Asp Glu Ala Ala Pro Pro Pro Arg
                160                 165                 170 tac agc ggt cgc atc gag ctc gcg cca gag gtt tac agg atg gac aag    639
Tyr Ser Gly Arg Ile Glu Leu Ala Pro Glu Val Tyr Arg Met Asp Lys
            175                 180                 185 atc aag gcg gag atg aag aac ggc gtg ctc aag gtg gtc gtg ccg aag    687
Ile Lys Ala Glu Met Lys Asn Gly Val Leu Lys Val Val Val Pro Lys
        190                 195                 200 gtg aag gag cag cag cgc aag gac gtg ttc caa gtc aac gtc gag tag    735
Val Lys Glu Gln Gln Arg Lys Asp Val Phe Gln Val Asn Val Glu
205                 210                 215 atgtttccaa atagaagcaa gtgccggtac gggatggagg attggagggg cactgccaaa    795
ctaggattcc tctctctcaa tctgatctgg attctggaat cagatttctc ttctttcatt    855
tttctcgtct atcttctatc agtatgaaat aagcaacgtc gcttcagttt tcgtgtcaag    915
gccggtggag tcgcctatgt ttattttatt ttctttgtat ttcctacctg gacacacgtt    975
ctctatgccg tgtttggttt ccgcagattt ttaaaatatg catgttcaaa ccc            1028

<210> SEQ ID NO: 2
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 2
ggaggggaga gtgtcgccat ggcttccatt gtcgcttcc                             39

<210> SEQ ID NO: 3
<211> LENGTH: 40
<212> TYPE: DNA
<213> ORGANISM: Artificial Sequence
<220> FEATURE:
<223> OTHER INFORMATION: Description of Artificial Sequence: Synthetic

<400> SEQUENCE: 3
```
gtgcccctcc aatcctggat cccttaccgg cacttgcttc            40

<210> SEQ ID NO: 4
<211> LENGTH: 829
<212> TYPE: DNA
<213> ORGANISM: Zea mays
<220> FEATURE:
<221> NAME/KEY: CDS
<222> LOCATION: (3)..(252)
<220> FEATURE:
<221> NAME/KEY: CDS
<222> LOCATION: (387)..(793)
<220> FEATURE:
<221> NAME/KEY: exon
<222> LOCATION: (1)..252
<220> FEATURE:
<221> NAME/KEY: exon
<222> LOCATION: (387)..(829)
<220> FEATURE:
<221> NAME/KEY: intron
<222> LOCATION: (253)..(386)
<220> FEATURE:
<221> NAME/KEY: gene
<222> LOCATION: (1)..(829)
<220> FEATURE:
<221> NAME/KEY: misc_feature
<222> LOCATION: (482)..(751)
<223> OTHER INFORMATION: Heat Shock Domain
<220> FEATURE:
<221> NAME/KEY: mRNA
<222> LOCATION: (1)..(252)
<220> FEATURE:
<221> NAME/KEY: mRNA
<222> LOCATION: (387)..(829)
<220> FEATURE:
<221> NAME/KEY: source
<222> LOCATION: (1)..(829)
<223> OTHER INFORMATION: Zea Mays L., Line B73
<220> FEATURE:
<221> NAME/KEY: transit_peptide
<222> LOCATION: (1)..(137)
<220> FEATURE:
<221> NAME/KEY: 3'UTR
<222> LOCATION: (794)..(829)
<220> FEATURE:
<221> NAME/KEY: 5'UTR
<222> LOCATION: (1)..(2)

<400> SEQUENCE: 4
ccatggcttc cattgtcgct tccaggaggg ccgttcctct agttcgcgct ctggagaagc      60
tcatcgcagc gtcctccgct cccgggactg gctccgccct caggccggtg cagtagccg     120 gcggcctccg cggctacaac accggcgctc cgctccgacg ctacgagggg gccgagtcgg    180
aagacgatag cgtccgcgag tacgatgggc ggcacggcgg ccgggactac gctgtgccca    240
gcctgttctc aggtagtcgt catcttcgct tcatgccaga cccatttgct ttgctctctc    300
aactctcaaa tgagatggtg gtgagactac atcgcttcga aatggctgtg ctgagtgctg    360
acttcgtctt gttggtccct gtccagatat tttccgtgat ccgcttagtg cgccgcacag    420
cattggccgc ctgctgaacc ttgtggacga cttgcggtg gcggcgccag gtcgtgcggt     480
gcgccgtggc tggaacgcga aggaggacga ggaggcgctg cacctgaggg tggacatgcc    540
aggcctgggg aaggagcacg tcaaggtgtg ggcggagcag aacagcctgg tgatcaaggg    600
cgagggcgag aaggaggata gcgaggacga ggccgccccg cccccgagat acagcggtcg    660
catcgggctc gcgccagagg tttacaggat ggacaagatc aaggcggaga tgaagaacgg    720
cgtgctcaag gtggtcgtgc cgaaggtgaa ggagcagcag cgcaaggacg tgttccaagt    780
caacgtcgag tagatgtttc caaatagaag caagtgccgg tagggatcc               829

<210> SEQ ID NO: 5
<211> LENGTH: 1163
<212> TYPE: DNA
<213> ORGANISM: Zea mays
<220> FEATURE:
<221> NAME/KEY: CDS
<222> LOCATION: (79)..(337)
<220> FEATURE:
<221> NAME/KEY: CDS
<222> LOCATION: (447)..(870)
<220> FEATURE:
<221> NAME/KEY: exon
<222> LOCATION: (1)..(337)
<220> FEATURE:
<221> NAME/KEY: exon
<222> LOCATION: (447)..(1163)
<220> FEATURE:
<221> NAME/KEY: gene
<222> LOCATION: (1)..(1163)
<220> FEATURE:
<221> NAME/KEY: intron
<222> LOCATION: (329)..(463)
<220> FEATURE:
<221> NAME/KEY: misc_feature
<222> LOCATION: (559)..(828)
<223> OTHER INFORMATION: Heat Shock Domain
<220> FEATURE:
<221> NAME/KEY: mRNA
<222> LOCATION: (1)..(337)
<220> FEATURE:
<221> NAME/KEY: mRNA
<222> LOCATION: (447)..(1163)
<220> FEATURE:
<221> NAME/KEY: Poly A_site
<222> LOCATION: (1163)..(1163)
<220> FEATURE:
<221> NAME/KEY: source
<222> LOCATION: (1)..(1163)
<223> OTHER INFORMATION: Zea Mays L., Line B73
<220> FEATURE:
<221> NAME/KEY: transit_peptide
<222> LOCATION: (79)..(213)
<220> FEATURE:
<221> NAME/KEY: 5'UTR
<222> LOCATION: (1)..(78)
<220> FEATURE:
<221> NAME/KEY: 3'UTR
<222> LOCATION: (871)..(1163)

<400> SEQUENCE: 5

```
ccacaacagc gaaggagaaa gcagaccaac ctagccaccc agggagaaag aggccaaaag      60
ggaggggaga gtgtcgtcat ggcttccatt gtcgcttcca ggagggccgt tcctctagtt     120
cgcgctctgg agaagctcat cgcagcgtcc tccgctcccg ggactggctc cgccctcagg     180
ccggtggcag tcgccggcgg cctccgcggc tacaacaccg cgctccgct  ccgacgctac     240 gaggggccg  agtcggaaga cgatagcgtc cgcgagtacg atgggcggca cggcggccgg     300
gactacgctg tgcccagcct gttctcaggt agtcgtcatc ttcgcttcat gccagaccca     360
tttgctttgc tctctcaact ctcaaatgag atggtggtga gactacatcg cttcgaaatg     420
gctgtgctga gtgctgactt cgtcttggtt ggtccctgtc cagatatttt ccgtgatccg     480
cttagtgcgc cgcacagcat tggccgcctg ctgaaccttg tggacgactt ggcggtggcg     540
gcgccaggtc gtgcggtgcg ccgtggctgg aacgcgaagg aggacgagga ggcgctgcac     600
ctgagggtgg acatgccagg cctggggaag gagcacgtca aggtgtgggc ggagcagaac     660
agcctggtga tcaagggcga gggcgagaag gaggatagcg aggacgaggc cgccccgcct     720
ccgagataca gcggtcgcat cgagctcgcg ccagaggttt acaggatgga caagatcaag     780
gcggagatga agaacggcgt gctcaaggtg gtcgtgccga aggtgaagga gcagcagcgc     840
```

-continued

```
aaggacgtgt tccaagtcaa cgtcgagtag atgtttccaa atagaagcaa gtgccggtac    900
gggatggagg attggagggg cactgccaaa ctaggattcc tctctctcaa tctgatctgg    960
attctggaat cagatttctc ttctttcatt tttctcgtct atcttctatc agtatgaaat   1020
aagcaacgtc gcttcagttt tcgtgtcaag gccggtggag tcgcctatgt ttattttatt   1080
ttctttgtat ttcctacctg gacacacgtt ctctatgccg tgtttggttt ccgcagattt   1140
ttaaaatatg catgttcaaa ccc                                           1163
```

```
<210> SEQ ID NO: 6
<211> LENGTH: 218
<212> TYPE: PRT
<213> ORGANISM: Zea mays
<220> FEATURE:
<221> NAME/KEY: PHOSPHORYLATION
<222> LOCATION: (59)
<220> FEATURE:
<221> NAME/KEY: TRANSIT
<222> LOCATION: (1)..(45)
<220> FEATURE:
<221> NAME/KEY: CHAIN
<222> LOCATION: (46)..(218)
<220> FEATURE:
<221> NAME/KEY: DOMAIN
<222> LOCATION: (116)..(205)
<223> OTHER INFORMATION: Heat Shock Domain
<220> FEATURE:
<221> NAME/KEY: HELIX
<222> LOCATION: (2)..(23)
<220> FEATURE:
<221> NAME/KEY: HELIX
<222> LOCATION: (107)..(115)
<220> FEATURE:
<221> NAME/KEY: HELIX
<222> LOCATION: (184)..(193)
<220> FEATURE:
<221> NAME/KEY: STRAND
<222> LOCATION: (141)..(147)
<223> OTHER INFORMATION: B-Sheet
<220> FEATURE:
<221> NAME/KEY: STRAND
<222> LOCATION: (150)..(154)
<223> OTHER INFORMATION: B-Sheet
<220> FEATURE:
<221> NAME/KEY: STRAND
<222> LOCATION: (197)..(201)
<223> OTHER INFORMATION: B-Sheet
<220> FEATURE:
<221> NAME/KEY: STRAND
<222> LOCATION: (213)..(217)
<223> OTHER INFORMATION: B-Sheet
<220> FEATURE:
<221> NAME/KEY: INIT_MET
<222> LOCATION: (1)..(218)

<400> SEQUENCE: 6
```

```
Met Ala Ser Ile Val Ala Ser Arg Arg Ala Val Pro Leu Val Arg Ala
 1               5                  10                  15

Leu Glu Lys Leu Ile Ala Ala Ser Ser Ala Pro Gly Thr Gly Ser Ala
            20                  25                  30

Leu Arg Pro Val Ala Val Ala Gly Gly Leu Arg Gly Tyr Asn Thr Gly
        35                  40                  45

Ala Pro Leu Arg Arg Tyr Glu Gly Ala Glu Ser Glu Asp Asp Ser Val
    50                  55                  60

Arg Glu Tyr Asp Gly Arg His Gly Gly Arg Asp Tyr Ala Val Pro Ser
65                  70                  75                  80

Leu Phe Ser Asp Ile Phe Arg Asp Pro Leu Ser Ala Pro His Ser Ile
                85                  90                  95
```

```
Gly Arg Leu Leu Asn Leu Val Asp Asp Leu Ala Val Ala Ala Pro Gly
            100                 105                 110

Arg Ala Val Arg Arg Gly Trp Asn Ala Lys Glu Asp Glu Glu Ala Leu
        115                 120                 125

His Leu Arg Val Asp Met Pro Gly Leu Gly Lys Glu His Val Lys Val
    130                 135                 140

Trp Ala Glu Gln Asn Ser Leu Val Ile Lys Gly Glu Gly Lys Glu
145                 150                 155                 160

Asp Ser Glu Asp Glu Ala Ala Pro Pro Arg Tyr Ser Gly Arg Ile
                165                 170                 175

Glu Leu Ala Pro Glu Val Tyr Arg Met Asp Lys Ile Lys Ala Glu Met
            180                 185                 190

Lys Asn Gly Val Leu Lys Val Val Pro Lys Val Lys Glu Gln Gln
        195                 200                 205

Arg Lys Asp Val Phe Gln Val Asn Val Glu
    210                 215
```

<210> SEQ ID NO: 7
<211> LENGTH: 657
<212> TYPE: DNA
<213> ORGANISM: Zea mays
<220> FEATURE:
<221> NAME/KEY: CDS
<222> LOCATION: (1)..(657)
<220> FEATURE:
<221> NAME/KEY: exon
<222> LOCATION: (1)..(250)
<220> FEATURE:
<221> NAME/KEY: exon
<222> LOCATION: (251)..(657)
<220> FEATURE:
<221> NAME/KEY: gene
<222> LOCATION: (1)..(657)
<220> FEATURE:
<221> NAME/KEY: misc_feature
<222> LOCATION: (345)..(615)
<223> OTHER INFORMATION: Heat Shock Domain
<220> FEATURE:
<221> NAME/KEY: mRNA
<222> LOCATION: (1)..(657)
<220> FEATURE:
<221> NAME/KEY: source
<222> LOCATION: (1)..(657)
<223> OTHER INFORMATION: Zea Mays L., Line B73
<220> FEATURE:
<221> NAME/KEY: transit_peptide
<222> LOCATION: (1)..(135)

<400> SEQUENCE: 7

```
atggcttcca ttgtcgcttc caggagggcc gttcctctag ttcgcgctct ggagaagctc      60
atcgcagcgt cctccgctcc cgggactggc tccgccctca ggccggtggc agtcgccggc     120
ggcctccgcg gctacaacac cggcgctccg ctccgacgct acgaggggc cgagtcggaa     180 gacgatagcg tccgcgagta cgatgggcgg cacggcggcc gggactacgc tgtgcccagc     240
ctgttctcag atattttccg tgatccgctt agtgcgccgc acagcattgg ccgcctgctg     300
aaccttgtgg acgacttggc ggtggcggcg ccaggtcgtg cggtgcgccg tggctggaac     360
gcgaaggagg acgaggaggc gctgcacctg agggtggaca tgccaggcct ggggaaggag     420
cacgtcaagg tgtgggcgga gcagaacagc ctggtgatca agggcgaggg cgagaaggag     480
```

```
gatagcgagg acgaggccgc cccgcctccg agatacagcg gtcgcatcga gctcgcgcca      540
gaggtttaca ggatggacaa gatcaaggcg gagatgaaga acggcgtgct caaggtggtc      600
gtgccgaagg tgaaggagca gcagcgcaag gacgtgttcc aagtcaacgt cgagtag        657
```